United States Patent
Duffy et al.

(10) Patent No.: US 11,452,599 B2
(45) Date of Patent: Sep. 27, 2022

(54) FLUID DIVERSION DEVICES FOR HYDRAULIC DELIVERY SYSTEMS AND ASSOCIATED METHODS

(71) Applicant: Twelve, Inc., Redwood City, CA (US)

(72) Inventors: Niall F. Duffy, Tuam (IE); Gavin Kenny, Galway (IE); Maurice Donoghue, Galway (IE)

(73) Assignee: Twelve, Inc., Redwood City, CA (US)

( * ) Notice: Subject to any disclaimer, the term of this patent is extended or adjusted under 35 U.S.C. 154(b) by 0 days.

(21) Appl. No.: 16/862,292

(22) Filed: Apr. 29, 2020

(65) Prior Publication Data
US 2020/0345489 A1 Nov. 5, 2020

Related U.S. Application Data

(60) Provisional application No. 62/842,252, filed on May 2, 2019.

(51) Int. Cl.
*A61F 2/24* (2006.01)
*A61F 2/48* (2006.01)

(52) U.S. Cl.
CPC ............ *A61F 2/2427* (2013.01); *A61F 2/484* (2021.08)

(58) Field of Classification Search
CPC ........ A61F 2/2427; A61F 2/484; A61F 2/958; A61F 2/954; A61F 2/9517; A61F 2/95; A61F 2002/9528; A61F 2002/9534; A61M 2039/0036–009; A61M 39/22–288; A61M 39/04–0693
See application file for complete search history.

(56) References Cited

U.S. PATENT DOCUMENTS

| | | |
|---|---|---|
| 4,388,735 A | 6/1983 | Ionescu et al. |
| 4,423,525 A | 1/1984 | Vallana et al. |
| 4,441,216 A | 4/1984 | Ionescu et al. |

(Continued)

FOREIGN PATENT DOCUMENTS

| | | |
|---|---|---|
| EP | 0224080 B1 | 7/1992 |
| EP | 1088529 B1 | 6/2005 |

(Continued)

OTHER PUBLICATIONS

International Search Report in corresponding International Application No. PCT/US2020/030645, dated Aug. 17, 2020, 2 pages.

*Primary Examiner* — Erich G Herbermann
(74) *Attorney, Agent, or Firm* — Medler Ferro Woodhouse & Mills PLLC

(57) ABSTRACT

A fluid diversion device configured in accordance with embodiments of the present technology can include, for example, a housing including channels configured to receive respective tubes, and a bore that extends laterally across the plurality of channels. The device can include an occlusion member disposed in the bore, where rotation of the occlusion member selectively occludes either a first subset of tubes or a second subset of tubes. The device can include an actuator that enables rotation of the occlusion member to a first position and a second position such that the first subset of tubes and the second subset of tubes are alternatively occluded in the first position or the second position for fluid communication in different directions relative to chambers of a delivery device operable to deploy and recapture the medical device.

24 Claims, 17 Drawing Sheets

(56) References Cited

U.S. PATENT DOCUMENTS

| | | |
|---|---|---|
| 4,629,459 A | 12/1986 | Ionescu et al. |
| 4,653,577 A | 3/1987 | Noda |
| 4,666,442 A | 5/1987 | Arru et al. |
| 4,679,556 A | 7/1987 | Lubock et al. |
| 4,758,151 A | 7/1988 | Arru et al. |
| 4,892,540 A | 1/1990 | Vallana |
| 5,002,567 A | 3/1991 | Bona et al. |
| 5,084,151 A | 1/1992 | Vallana et al. |
| 5,104,406 A | 4/1992 | Curcio et al. |
| 5,370,684 A | 12/1994 | Vallana et al. |
| 5,387,247 A | 2/1995 | Vallana et al. |
| 5,713,953 A | 2/1998 | Vallana et al. |
| 5,873,812 A | 2/1999 | Ciana et al. |
| 7,220,277 B2 | 5/2007 | Arru et al. |
| 7,510,575 B2 | 3/2009 | Spenser et al. |
| 7,857,845 B2 | 12/2010 | Stacchino et al. |
| 7,993,392 B2 | 8/2011 | Righini et al. |
| 8,006,535 B2 | 8/2011 | Righini et al. |
| 8,034,103 B2 | 10/2011 | Burriesci et al. |
| 8,057,539 B2 | 11/2011 | Ghione et al. |
| 8,070,799 B2 | 12/2011 | Righini et al. |
| 8,109,996 B2 | 2/2012 | Stacchino et al. |
| 8,114,154 B2 | 2/2012 | Righini et al. |
| 8,353,953 B2 | 1/2013 | Giannetti et al. |
| 8,403,982 B2 | 3/2013 | Giannetti et al. |
| 8,470,024 B2 | 6/2013 | Ghione et al. |
| 8,486,137 B2 | 6/2013 | Suri et al. |
| 8,475,521 B2 | 7/2013 | Suri et al. |
| 8,512,397 B2 | 8/2013 | Rolando et al. |
| 8,539,662 B2 | 9/2013 | Stacchino et al. |
| 8,540,768 B2 | 9/2013 | Stacchino et al. |
| 8,640,521 B2 | 2/2014 | Righini et al. |
| 8,715,207 B2 | 5/2014 | Righini et al. |
| 8,808,366 B2 | 8/2014 | Braido et al. |
| 8,808,367 B2 | 8/2014 | Suri et al. |
| 8,834,563 B2 | 9/2014 | Righini |
| 8,840,661 B2 | 9/2014 | Manasse |
| 8,920,492 B2 | 12/2014 | Stacchino et al. |
| 9,050,188 B2 | 6/2015 | Schweich, Jr. et al. |
| 9,056,088 B2 | 6/2015 | Righini et al. |
| 9,114,010 B2 | 8/2015 | Gaschino et al. |
| 9,138,314 B2 | 9/2015 | Rolando et al. |
| 9,149,207 B2 | 10/2015 | Sauter et al. |
| 9,161,836 B2 | 10/2015 | Rolando et al. |
| 9,168,105 B2 | 10/2015 | Giannetti et al. |
| 9,186,249 B2 | 11/2015 | Rolando et al. |
| 9,204,819 B2 | 12/2015 | Grunwald et al. |
| 9,248,017 B2 | 2/2016 | Rolando et al. |
| 9,289,289 B2 | 3/2016 | Rolando et al. |
| 9,339,207 B2 | 5/2016 | Grunwald et al. |
| 9,358,105 B2 | 6/2016 | Marchisio et al. |
| 9,421,094 B2 | 8/2016 | Schweich, Jr. et al. |
| 9,433,514 B2 | 9/2016 | Quadri |
| 9,480,559 B2 | 11/2016 | Vidlund et al. |
| 9,486,313 B2 | 11/2016 | Stacchino et al. |
| 9,504,835 B2 | 11/2016 | Graindorge |
| 9,579,198 B2 * | 2/2017 | Deem .................. A61F 2/95 |
| 9,700,413 B2 | 7/2017 | Ruyra Baliarda et al. |
| 9,750,607 B2 | 9/2017 | Ganesan et al. |
| 9,788,931 B2 | 10/2017 | Giordano et al. |
| 9,833,315 B2 | 12/2017 | Vidlund et al. |
| 9,848,981 B2 | 12/2017 | Suri et al. |
| 9,867,695 B2 | 1/2018 | Stacchino et al. |
| 9,895,223 B2 | 2/2018 | Stacchino et al. |
| 9,895,225 B2 | 2/2018 | Rolando et al. |
| 9,918,841 B2 | 3/2018 | Righini et al. |
| 9,974,647 B2 | 5/2018 | Ganesan et al. |
| 10,058,313 B2 | 8/2018 | Manasse |
| 10,065,032 B2 | 9/2018 | Ollivier |
| 10,098,733 B2 | 10/2018 | Righini |
| 10,117,741 B2 | 11/2018 | Schweich, Jr. et al. |
| 10,143,550 B2 | 12/2018 | Achiluzzi |
| 10,213,301 B2 | 2/2019 | Ganesan et al. |
| 10,245,141 B2 | 4/2019 | Ghione et al. |
| 10,265,166 B2 | 4/2019 | Schweich, Jr. et al. |
| 10,285,810 B2 | 5/2019 | Schweich, Jr. et al. |
| 10,449,039 B2 | 10/2019 | Ganesan et al. |
| 2002/0188350 A1 | 12/2002 | Arru et al. |
| 2003/0120296 A1 * | 6/2003 | Shturman ............ A61M 3/0208 606/167 |
| 2008/0147181 A1 | 6/2008 | Ghione et al. |
| 2008/0262603 A1 | 10/2008 | Giaquinta et al. |
| 2009/0105794 A1 | 4/2009 | Ziarno et al. |
| 2010/0076376 A1 | 3/2010 | Manasse et al. |
| 2012/0303048 A1 | 11/2012 | Manasse |
| 2013/0123915 A1 | 5/2013 | Giannetti et al. |
| 2013/0231735 A1 | 9/2013 | Deem et al. |
| 2013/0338766 A1 | 12/2013 | Hastings et al. |
| 2014/0207011 A1 | 7/2014 | Righini et al. |
| 2016/0158415 A1 | 6/2016 | Strasly et al. |
| 2018/0161585 A1 | 6/2018 | Ollivier |
| 2018/0214263 A1 | 8/2018 | Rolando et al. |
| 2018/0221147 A1 | 8/2018 | Ganesan et al. |
| 2018/0235753 A1 | 8/2018 | Ganesan et al. |
| 2018/0325660 A1 | 11/2018 | Mauch et al. |
| 2018/0338832 A1 | 11/2018 | Ganesan et al. |
| 2019/0000618 A1 | 1/2019 | Schweich, Jr. et al. |
| 2019/0029814 A1 | 1/2019 | Schweich, Jr. et al. |
| 2019/0142581 A1 | 5/2019 | Maiso et al. |
| 2019/0183641 A1 | 6/2019 | Ganesan et al. |
| 2019/0192292 A1 | 6/2019 | Schweich, Jr. et al. |

FOREIGN PATENT DOCUMENTS

| | | |
|---|---|---|
| EP | 1967164 A2 | 9/2008 |
| EP | 2033581 A1 | 3/2009 |
| EP | 2014257 B1 | 9/2010 |
| EP | 2033597 B1 | 3/2011 |
| EP | 2165651 B1 | 8/2011 |
| EP | 1719476 B1 | 11/2011 |
| EP | 2399527 A1 | 12/2011 |
| EP | 2399527 A8 | 3/2012 |
| EP | 2229921 B1 | 11/2014 |
| EP | 2861186 A2 | 4/2015 |
| EP | 2250976 B1 | 8/2015 |
| EP | 3050541 A1 | 8/2016 |
| EP | 3102152 A1 | 12/2016 |
| WO | 97/14470 A1 | 4/1997 |
| WO | 2015118464 A1 | 8/2015 |
| WO | 2017/173331 A1 | 10/2017 |
| WO | 2018/167536 A1 | 9/2018 |
| WO | 2018/222684 A1 | 12/2018 |
| WO | 2019/069145 A1 | 4/2019 |
| WO | 2019/209927 A1 | 10/2019 |

* cited by examiner

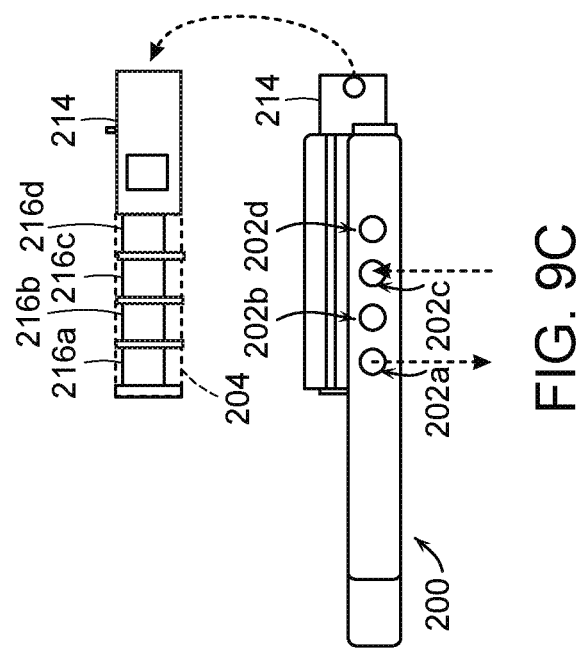
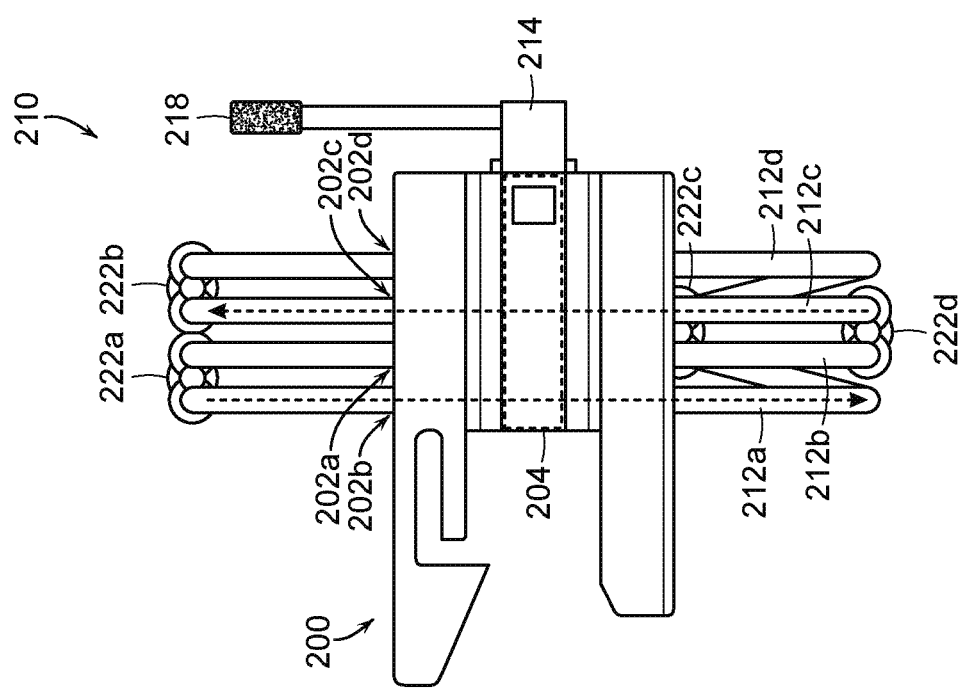

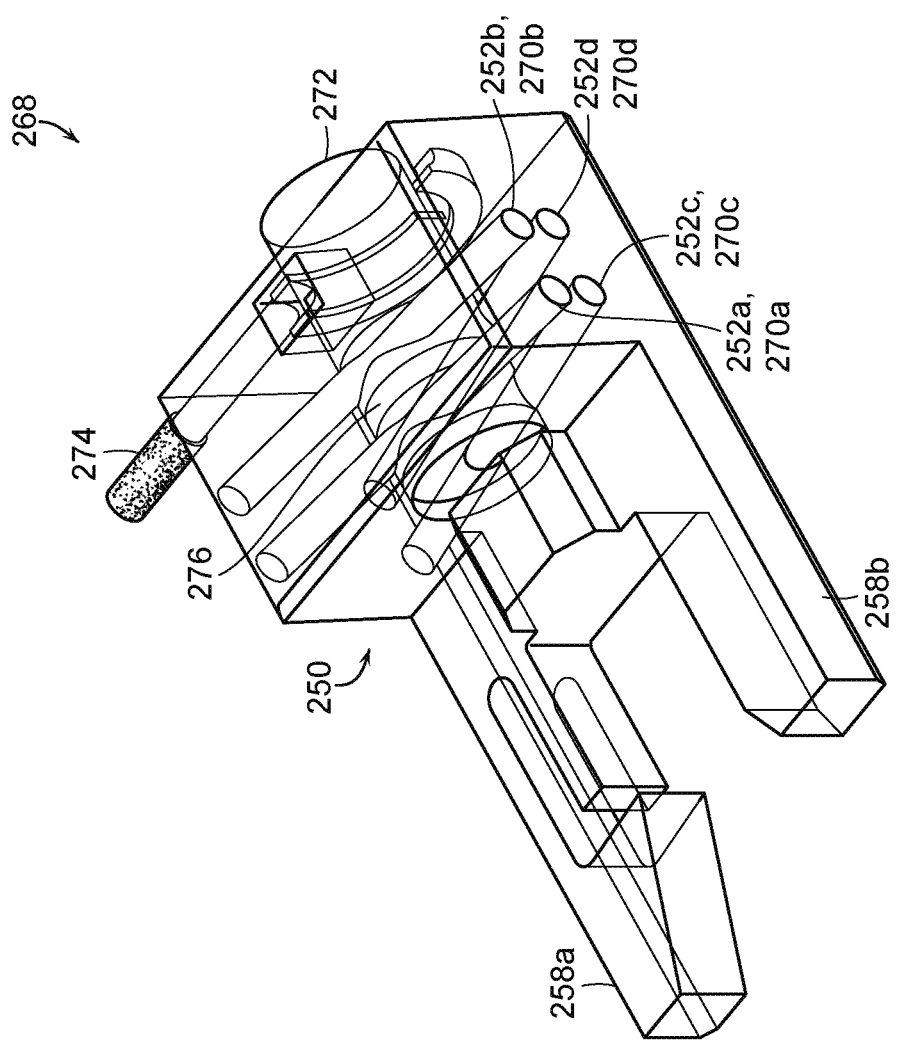

FLUID DIVERSION DEVICES FOR HYDRAULIC DELIVERY SYSTEMS AND ASSOCIATED METHODS

This application claims the benefit of U.S. Provisional Patent Application No. 62/842,252, entitled, "FLUID DIVERSION DEVICES FOR HYDRAULIC DELIVERY SYSTEMS AND ASSOCIATED METHODS," filed May 2, 2019, the entire content of which is incorporated herein by reference.

TECHNICAL FIELD

The present technology relates generally to hydraulic delivery systems for implanting medical devices. In particular, several embodiments of the present technology are related to cam-based fluid diversion devices for hydraulic delivery systems for deploying medical and associated methods.

BACKGROUND

Heart valves can be affected by several conditions. For example, mitral valves can be affected by mitral valve regurgitation, mitral valve prolapse and mitral valve stenosis. Mitral valve regurgitation is abnormal leaking of blood from the left ventricle into the left atrium caused by a disorder of the heart in which the leaflets of the mitral valve fail to coapt into apposition at peak contraction pressures. The mitral valve leaflets may not coapt sufficiently because heart diseases often cause dilation of the heart muscle, which in turn enlarges the native mitral valve annulus to the extent that the leaflets do not coapt during systole. Abnormal backflow can also occur when the papillary muscles are functionally compromised due to ischemia or other conditions. More specifically, as the left ventricle contracts during systole, the affected papillary muscles do not contract sufficiently to effect proper closure of the leaflets.

Mitral valve prolapse is a condition when the mitral leaflets bulge abnormally up into the left atrium. This can cause irregular behavior of the mitral valve and lead to mitral valve regurgitation. The leaflets may prolapse and fail to coapt because the tendons connecting the papillary muscles to the inferior side of the mitral valve leaflets (chordae tendineae) may tear or stretch. Mitral valve stenosis is a narrowing of the mitral valve orifice that impedes filling of the left ventricle in diastole.

Mitral valve regurgitation is often treated using diuretics and/or vasodilators to reduce the amount of blood flowing back into the left atrium. Surgical approaches (e.g., open and intravascular) for either the repair or replacement of the valve have also been used to treat mitral valve regurgitation. For example, typical repair techniques involve cinching or resecting portions of the dilated annulus. Cinching, for example, includes implanting annular or peri-annular rings that are generally secured to the annulus or surrounding tissue. Other repair procedures suture or clip the valve leaflets into partial apposition with one another.

Alternatively, more invasive procedures replace the entire valve itself by implanting mechanical valves or biological tissue into the heart in place of the native mitral valve. These invasive procedures conventionally require large open thoracotomies and are thus very painful, have significant morbidity, and require long recovery periods. Moreover, with many repair and replacement procedures, the durability of the devices or improper sizing of annuloplasty rings or replacement valves may cause additional problems for the patient. Repair procedures also require a highly skilled cardiac surgeon because poorly or inaccurately placed sutures may affect the success of procedures.

Less invasive approaches to aortic valve replacement have been implemented recently. Examples of pre-assembled, percutaneous prosthetic valves include, e.g., the CoreValve Revalving® System from Medtronic/Corevalve Inc. (Irvine, Calif., USA) and the Edwards-Sapien® Valve from Edwards Lifesciences (Irvine, Calif., USA). Both valve systems include an expandable frame and a tri-leaflet bio-prosthetic valve attached to the expandable frame. The aortic valve is substantially symmetric, circular, and has a muscular annulus. The expandable frames in aortic applications have a symmetric, circular shape at the aortic valve annulus to match the native anatomy, but also because tri-leaflet prosthetic valves require circular symmetry for proper coaptation of the prosthetic leaflets. Thus, aortic valve anatomy lends itself to an expandable frame housing a replacement valve since the aortic valve anatomy is substantially uniform, symmetric, and fairly muscular. Other heart valve anatomies, however, are not uniform, symmetric or sufficiently muscular, and thus transvascular aortic valve replacement devices may not be well suited for other types of heart valves.

Therefore, during a mitral valve replacement procedure, it is critical yet challenging to deploy an implant in a timely manner and targeted position due to the complex anatomy of a heart. Accordingly, it is desirable for delivery systems to enable complex operations in a flexible manner to facilitate targeted delivery of an implant with minimal time and procedural steps by alleviating the physical and cognitive burdens on clinicians operating the delivery systems during replacement procedures.

SUMMARY

In some examples, the disclosure describes a fluid diversion device for controlling fluid flow in a delivery system to deploy a prosthetic heart valve device, the fluid diversion device comprising: a housing including a first side, a second side, a bore, and a plurality of channels traversing the housing from the first side through the bore to the second side, wherein the plurality of channels are configured to receive a corresponding plurality of tubes that extend from the first side through the bore to the second side of the housing, and wherein the bore extends laterally across the plurality of channels; an occlusion member disposed in the bore, wherein rotation of the occlusion member enables selective occlusion of either a first subset of tubes or a second subset of tubes disposed in the plurality of channels; and an actuator operably coupled to the occlusion member to enable selective positioning of the occlusion member in at least a first position that occludes the first subset of tubes and a second position that occludes the second subset of tubes for fluid communication in different directions relative to a first chamber and a second chamber of a delivery device to cause deployment and recapture of the prosthetic heart valve device.

In some examples, the disclosure describes a system for delivering a prosthetic heart valve device into a heart of a patient, the system comprising: an elongated catheter body including a delivery control component that is hydraulically driven to deploy and recapture the prosthetic heart valve device relative to the heart of the patient; a plurality of chambers including a first chamber and a second chamber operable to receive or expel fluid to hydraulically drive deployment and recapture of the prosthetic heart valve device; and a fluid diversion device including: a housing including a first side, a second side, a bore, and a plurality of channels traversing the housing from the first side through the bore to the second side, wherein the plurality of channels is configured to receive a corresponding plurality of tubes that extend from the first side through the bore to the second side of the housing, and wherein the bore extends laterally across the plurality of channels, an occlusion member disposed in the bore, wherein rotation of the occlusion member enables selective occlusion of either a first subset of tubes or a second subset of tubes disposed in the plurality of channels, and an actuator operably coupled to the occlusion member to enable selective positioning of the occlusion member in at least a first position that occludes the first subset of tubes and a second position that occludes the second subset of tubes for fluid communication in different directions relative to the first chamber and the second chamber to cause deployment and recapture of the prosthetic heart valve device.

In some examples, the disclosure describes a fluid diversion device for controlling fluid flow in a delivery system to deploy a medical device, the fluid diversion device comprising: a housing including a plurality of channels configured to receive a corresponding plurality of tubes, and a bore that extends laterally across the plurality of channels; an occlusion member disposed in the bore, wherein rotation of the occlusion member selectively occludes either a first subset of tubes from the plurality of tubes or a second subset of tubes from the plurality of tubes; and an actuator configured to enable rotation of the occlusion member to at least a first position and a second position such that the first subset of tubes and the second subset of tubes are alternatively occluded in the first position or the second position for fluid communication in different directions relative to a plurality of chambers of a delivery device operable to deploy and recapture the medical device.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent. The headings provided herein are for convenience only.

FIG. 9B is a top view of the fluid diversion device of FIG. 9A in a first configuration in accordance with embodiments of the present technology.

FIG. 9C is a side view of the fluid diversion device of FIG. 9B in the first configuration.

FIG. 12B is a partially transparent isomeric view of the fluid diversion device of FIG. 12A in a first configuration in accordance with embodiments of the present technology.

DETAILED DESCRIPTION

Figure 1:
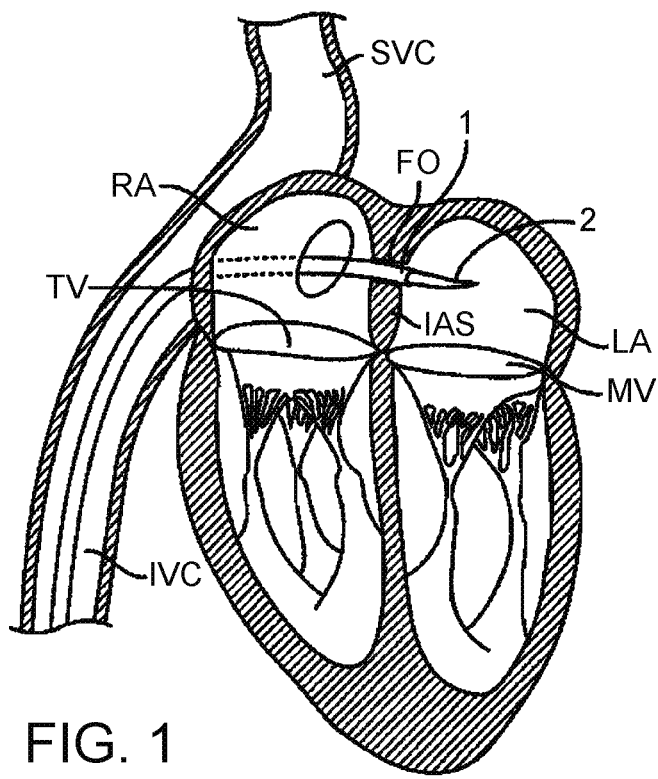
FIG. 1 is a schematic, cross-sectional illustration of the heart showing an antegrade approach to the native mitral valve from the venous vasculature in accordance with various embodiments of the present technology.

The present technology is generally directed to fluid diversion devices of hydraulic delivery systems and associated methods. Specific details of several embodiments of the present technology are described herein with reference to FIGS. 1-12I. Although many of the embodiments are described with respect to devices, systems, and methods for delivering prosthetic heart valve devices to a native mitral valve, other applications and other embodiments in addition to those described herein are within the scope of the present technology. For example, at least some embodiments of the present technology may be useful for delivering prosthetic valves to other sites, such as the tricuspid valve or the aortic valve. In addition, the present technology may be used to deliver cardiac valve repair devices and/or other medical devices to target sites within the body. It should be noted that other embodiments in addition to those disclosed herein are within the scope of the present technology. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

With regard to the terms "distal" and "proximal" within this description, unless otherwise specified, the terms can reference relative positions of portions of a prosthetic valve device and/or an associated delivery device with reference to an operator and/or a location in the vasculature or heart. For example, in referring to a delivery catheter suitable to deliver and position various prosthetic valve devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a prosthetic heart valve device, the terms "proximal" and "distal" can refer to the location of portions of the device with respect to the direction of blood flow. For example, proximal can refer to an upstream position or a location where blood flows into the device (e.g., inflow region), and distal can refer to a downstream position or a location where blood flows out of the device (e.g., outflow region).

Several embodiments of the present technology are directed to fluid diversion devices of delivery systems for mitral valve replacement devices that address the unique challenges of percutaneously replacing native mitral valves and are well-suited to be recaptured in a percutaneous delivery device after being partially deployed for repositioning or removing the device. Compared to replacing aortic valves, percutaneous mitral valve replacement faces unique anatomical obstacles that render percutaneous mitral valve replacement significantly more challenging than aortic valve replacement. First, unlike relatively symmetric and uniform aortic valves, the mitral valve annulus has a non-circular D-shape or kidney-like shape, with a non-planar, saddle-like geometry often lacking symmetry. The complex and highly variable anatomy of mitral valves makes it difficult to design a mitral valve prosthesis that conforms well to the native mitral annulus of specific patients. As a result, the prosthesis may not fit well with the native leaflets and/or annulus, which can leave gaps that allow backflow of blood to occur. For example, placement of a cylindrical valve prosthesis in a native mitral valve may leave gaps in commissural regions of the native valve through which perivalvular leaks may occur.

Current prosthetic valves developed for percutaneous aortic valve replacement are unsuitable for use in mitral valves. First, many of these devices require a direct, structural connection between the stent-like structure that contacts the annulus and/or leaflets and the prosthetic valve. In several devices, the stent posts which support the prosthetic valve also contact the annulus or other surrounding tissue. These types of devices directly transfer the forces exerted by the tissue and blood as the heart contracts to the valve support and the prosthetic leaflets, which in turn distorts the valve support from its desired cylindrical shape. This is a concern because most cardiac replacement devices use tri-leaflet valves, which require a substantially symmetric, cylindrical support around the prosthetic valve for proper opening and closing of the three leaflets over years of life. As a result, when these devices are subject to movement and forces from the annulus and other surrounding tissues, the prostheses may be compressed and/or distorted causing the prosthetic leaflets to malfunction. Moreover, a diseased mitral annulus is much larger than any available prosthetic aortic valve. As the size of the valve increases, the forces on the valve leaflets increase dramatically, so simply increasing the size of an aortic prosthesis to the size of a dilated mitral valve annulus would require dramatically thicker, taller leaflets, and might not be feasible.

In addition to its irregular, complex shape, which changes size over the course of each heartbeat, the mitral valve annulus lacks a significant amount of radial support from surrounding tissue. Compared to aortic valves, which are completely surrounded by fibro-elastic tissue that provides sufficient support for anchoring a prosthetic valve, mitral valves are bound by muscular tissue on the outer wall only. The inner wall of the mitral valve anatomy is bound by a thin vessel wall separating the mitral valve annulus from the inferior portion of the aortic outflow tract. As a result, significant radial forces on the mitral annulus, such as those imparted by an expanding stent prosthesis, could lead to collapse of the inferior portion of the aortic tract. Moreover, larger prostheses exert more force and expand to larger dimensions, which exacerbates this problem for mitral valve replacement applications.

The chordae tendineae of the left ventricle may also present an obstacle in deploying a mitral valve prosthesis. Unlike aortic valves, mitral valves have a maze of cordage under the leaflets in the left ventricle that restrict the movement and position of a deployment catheter and the replacement device during implantation. As a result, deploying, positioning, and anchoring a valve replacement device on the ventricular side of the native mitral valve annulus is complicated.

During transcatheter mitral valve replacement (e.g., delivered via a transfemoral or transapical approach), it is critical to deploy the valve replacement device in a timely manner and in a correct position relative to the native annulus, leaflets, left atrium, and left ventricular outflow tract. Accordingly, it is desirable for a delivery system to enable flexible deployment and/or recapture of a valve replacement device with minimal time and procedural steps. However, conventional delivery systems include burdensome fluid diversion devices such as an arrangement of multiple interconnected three-way stopcocks that must be separately adjusted to desired positions to change the direction of a delivery from deploy to recapture, or vice versa. This arrangement can be confusing and require excessive additional time such that use of conventional fluid diversion devices poses a physical and cognitive burden on a clinician, which increases the risks associated with replacement procedures.

Embodiments of the present technology provide systems, methods and apparatus to treat heart valves of the body, such as the mitral valve, that address the challenges associated with the anatomy of the mitral valve and provide for repositioning and removal of a valve replacement device. The disclosed embodiments include a fluid diversion device that can perform complex operations to flexibly place a valve replacement device in a target position, in a timely manner, by reducing the physical and cognitive burdens on a clinician to operate the fluid diversion device.

The disclosed embodiments overcome the aforementioned drawbacks with fluid diversion devices of dual-hydraulic delivery systems that can readily and reliably deploy and/or recapture valve replacement devices. For example, a fluid diversion device of the disclosed embodiments can implement a cam mechanism that can be rotated with a handle to switch between deploy and recapture configurations. The disclosed embodiments thus obviate the need for an arrangement of multiple interconnected three-way stopcocks, which saves the clinician time by simplifying operations for changing the delivery device from deploy to recapture configurations, or vice versa.

The disclosed systems and methods enable a percutaneous approach using a catheter delivered intravascularly through a vein or artery into the heart, or through a cannula inserted through the heart wall. For example, the systems and methods are particularly well-suited for trans-septal and transapical approaches, but can also provide trans-atrial and direct aortic delivery of a prosthetic replacement valve to a target location in the heart. Additionally, the embodiments of the systems and methods as described herein can be combined with many known surgeries and procedures, such as known methods of accessing the valves of the heart (e.g., the mitral valve or triscuspid valve) with antegrade or retrograde approaches, and combinations thereof.

The disclosed fluid diversion devices facilitate controlled delivery of a prosthetic heart valve device using transapical or trans-septal delivery approaches and allow resheathing of the prosthetic heart valve device after partial deployment of the device to reposition and/or remove the device. The disclosed fluid diversion devices are coupled to two fluid chambers that are interchangeably filled with fluid and drained of fluid to initiate deployment and resheathing of the prosthetic device. This facilitates hydraulic control and power for both proximal and distal movement of a delivery capsule housing that provides for controlled delivery of the prosthetic heart valve device and inhibits uncontrolled movement of the delivery system resulting from forces associated with expansion of the prosthetic heart valve device (e.g., axial jumping, self-ejection). In addition, the hydraulic delivery systems disclosed herein can inhibit longitudinal translation of the prosthetic heart valve device relative to the treatment site while the prosthetic heart valve device moves between the containment configuration (i.e., fully recaptured) and the deployment configuration. This allows the clinician to accurately position the sheathed prosthetic heart valve device at the desired target site for deployment, and then deploy the device at that target site without needing to compensate for any axial movement caused by deployment.

To better understand the structure and operation of valve replacement devices in accordance with the present technology, it is helpful to first understand approaches for implanting the devices. The mitral valve or other type of atrioventricular valve can be accessed through the patient's vasculature in a percutaneous manner. By percutaneous, it is meant that a location of the vasculature remote from the heart is accessed through the skin, typically using a surgical cut-down procedure or a minimally invasive procedure, such as using needle access through, for example, the Seldinger technique. The ability to percutaneously access the remote vasculature is well known and described in patent and medical literature. Depending on the point of vascular access, access to the mitral valve may be antegrade and may rely on entry into the left atrium by crossing the inter-atrial septum (e.g., a trans-septal approach). Alternatively, access to the mitral valve can be retrograde where the left ventricle is entered through the aortic valve. Access to the mitral valve may also be achieved using a cannula via a transapical approach. Depending on the approach, the interventional tools and supporting catheter(s) may be advanced to the heart intravascularly and positioned adjacent the target cardiac valve in a variety of manners, as described herein.

FIG. 1 illustrates a stage of a trans-septal approach for implanting a valve replacement device. In a trans-septal approach, access is via the inferior vena cava IVC or superior vena cava SVC, through the right atrium RA, across the inter-atrial septum IAS, and into the left atrium LA above the mitral valve MV. As shown in FIG. 1, a catheter 1 having a needle 2 moves from the inferior vena cava IVC into the right atrium RA. Once the catheter 1 reaches the anterior side of the inter-atrial septum IAS, the needle 2 advances so that it penetrates through the septum, for example at the fossa ovalis FO or the foramen ovale into the left atrium LA. At this point, a guidewire replaces the needle 2 and the catheter 1 is withdrawn.

Figure 2:
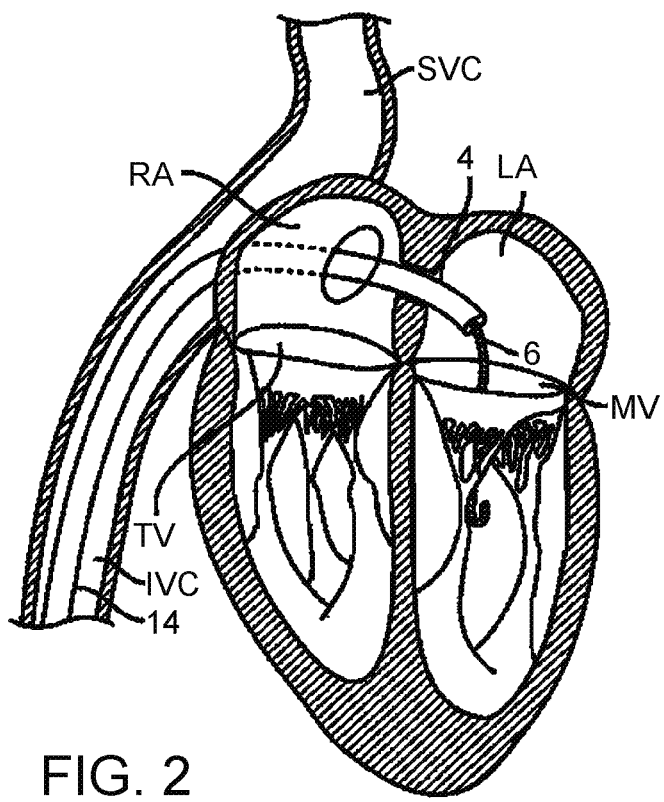
FIG. 2 is a schematic, cross-sectional illustration of the heart showing access through the inter-atrial septum (IAS) maintained by the placement of a guide catheter over a guidewire in accordance with various embodiments of the present technology.

FIG. 2 illustrates a subsequent stage of a trans-septal approach in which guidewire 6 and guide catheter 4 pass through the inter-atrial septum IAS. The guide catheter 4 provides access to the mitral valve for implanting a valve replacement device in accordance with the technology.

In an alternative antegrade approach (not shown), surgical access may be obtained through an intercostal incision, preferably without removing ribs, and a small puncture or incision may be made in the left atrial wall. A guide catheter passes through this puncture or incision directly into the left atrium, sealed by a purse string-suture.

The antegrade or trans-septal approach to the mitral valve, as described above, can be advantageous in many respects. For example, antegrade approaches will usually enable more precise and effective centering and stabilization of the guide catheter and/or prosthetic valve device. The antegrade approach may also reduce the risk of damaging the chordae tendinae or other subvalvular structures with a catheter or other interventional tool. Additionally, the antegrade approach may decrease risks associated with crossing the aortic valve as in retrograde approaches. This can be particularly relevant to patients with prosthetic aortic valves, which cannot be crossed at all or without substantial risk of damage.

Figure 3:
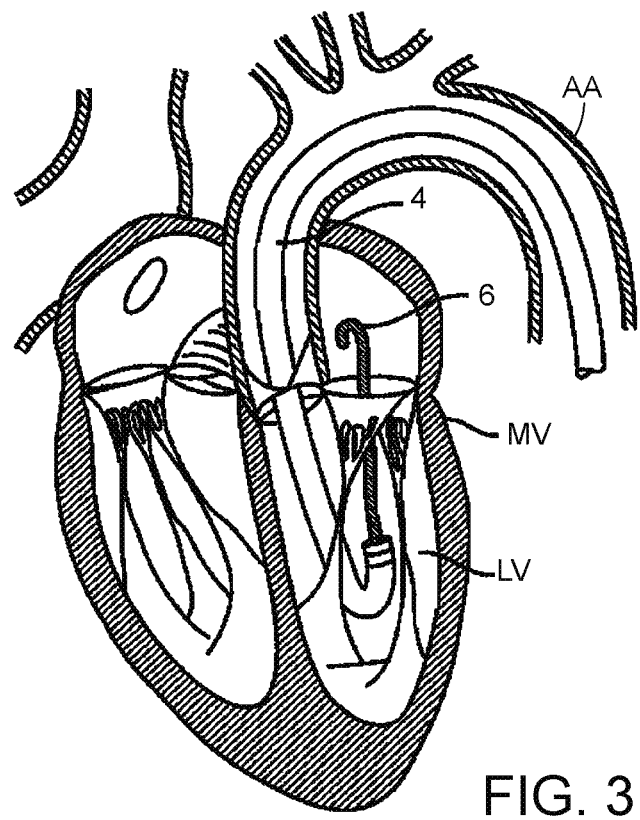
FIG. 3 is a schematic, cross-sectional illustration of the heart showing an aspect of a retrograde approach to the native mitral valve through the aortic valve and arterial vasculature in accordance with various embodiments of the present technology.
Figure 4:
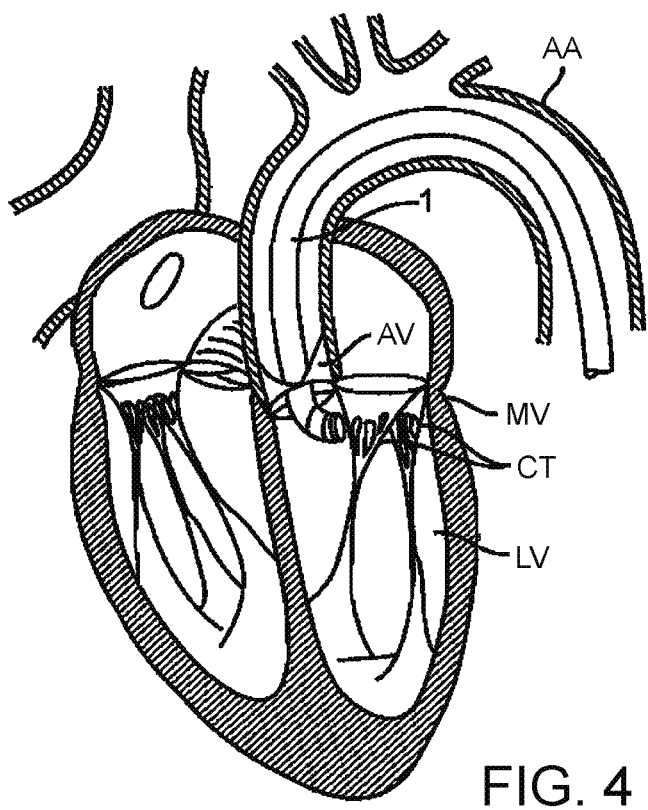
FIG. 4 is a schematic, cross-sectional illustration of the heart showing another aspect of a retrograde approach to the native mitral valve through the aortic valve and arterial vasculature in accordance with various embodiments of the present technology.

FIGS. 3 and 4 show examples of a retrograde approaches to access the mitral valve. Access to the mitral valve MV may be achieved from the aortic arch AA, across the aortic valve AV, and into the left ventricle LV below the mitral valve MV. The aortic arch AA may be accessed through a conventional femoral artery access route or through more direct approaches via the brachial artery, axillary artery, radial artery, or carotid artery. Such access may be achieved with the use of a guidewire 6. Once in place, a guide catheter 4 may be tracked over the guidewire 6. Alternatively, a surgical approach may be taken through an incision in the chest, preferably intercostally without removing ribs, and placing a guide catheter through a puncture in the aorta itself. The guide catheter 4 affords subsequent access to permit placement of the prosthetic valve device, as described in more detail herein. Retrograde approaches advantageously do not need a trans-septal puncture. Cardiologists also more commonly use retrograde approaches, and thus retrograde approaches are more familiar.

Figure 5:
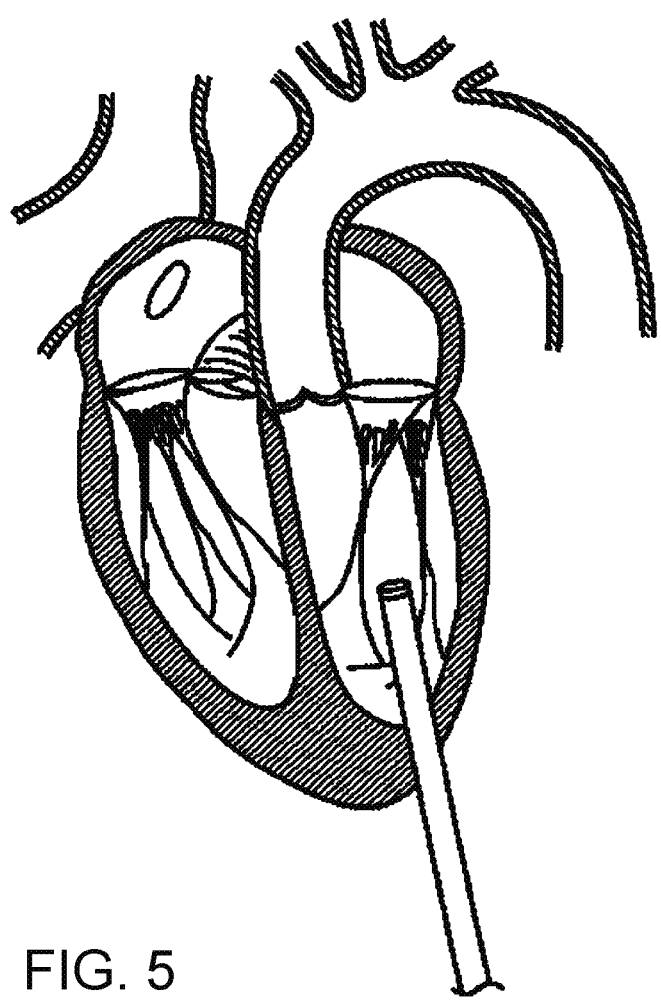
FIG. 5 is a schematic, cross-sectional illustration of the heart showing an approach to the native mitral valve using a transapical puncture in accordance with various embodiments of the present technology.

FIG. 5 shows a transapical approach via a transapical puncture. In this approach, access to the heart is via a thoracic incision, which can be a conventional open thoracotomy or sternotomy, or a smaller intercostal or subxyphoid incision or puncture. An access cannula is then placed through a puncture in the wall of the left ventricle at or near the apex of the heart. The catheters and prosthetic devices of the invention may then be introduced into the left ventricle through this access cannula. The transapical approach provides a shorter, straighter, and more direct path to the mitral or aortic valve. Further, because it does not involve intravascular access, the transapical approach does not require training in interventional cardiology to perform the catheterizations required in other percutaneous approaches.

During transcatheter heart valve replacement (e.g., delivered via transfemoral or transapical approach), it is important to deploy the prosthetic heart valve device in a controlled and efficient manner at the correct target position relative to the native annulus, leaflets, left atrium, and the left ventricular outflow tract (LVOT). For example, the hydraulically controlled movement of a delivery capsule can reduce, limit, or substantially eliminate uncontrolled deployment of the prosthetic heart valve device caused by forces associated with the expanding heart valve device. Delivery systems can also use hydraulically controlled movement to resheathe a partially or fully-expanded heart valve device to allow for repositioning of the heart valve device relative to the native anatomy and/or recapture of the device for removal from the body.

The fluid diversion devices described herein facilitate changing from deployment and recapture configurations in an efficient manner. For example, instead of requiring physical manipulation of multiple handles of multiple interconnected stopcocks in a complex pattern, the disclosed fluid diversion devices require less manual adjustments to change the direction of fluid flow within the delivery system and switch between deploy and recapture configurations. In some embodiments, for example, a fluid diversion device has a handle that can rotate an occlusion mechanism to change the fluid diversion device between two positions to initiate deployment or recapture of a prosthetic heart valve device. As such, the disclosed devices can simplify the process for performing complex operations to switch between deployment and recapture configurations and enhance the efficiency and ease of use of the delivery system.

Figure 6:
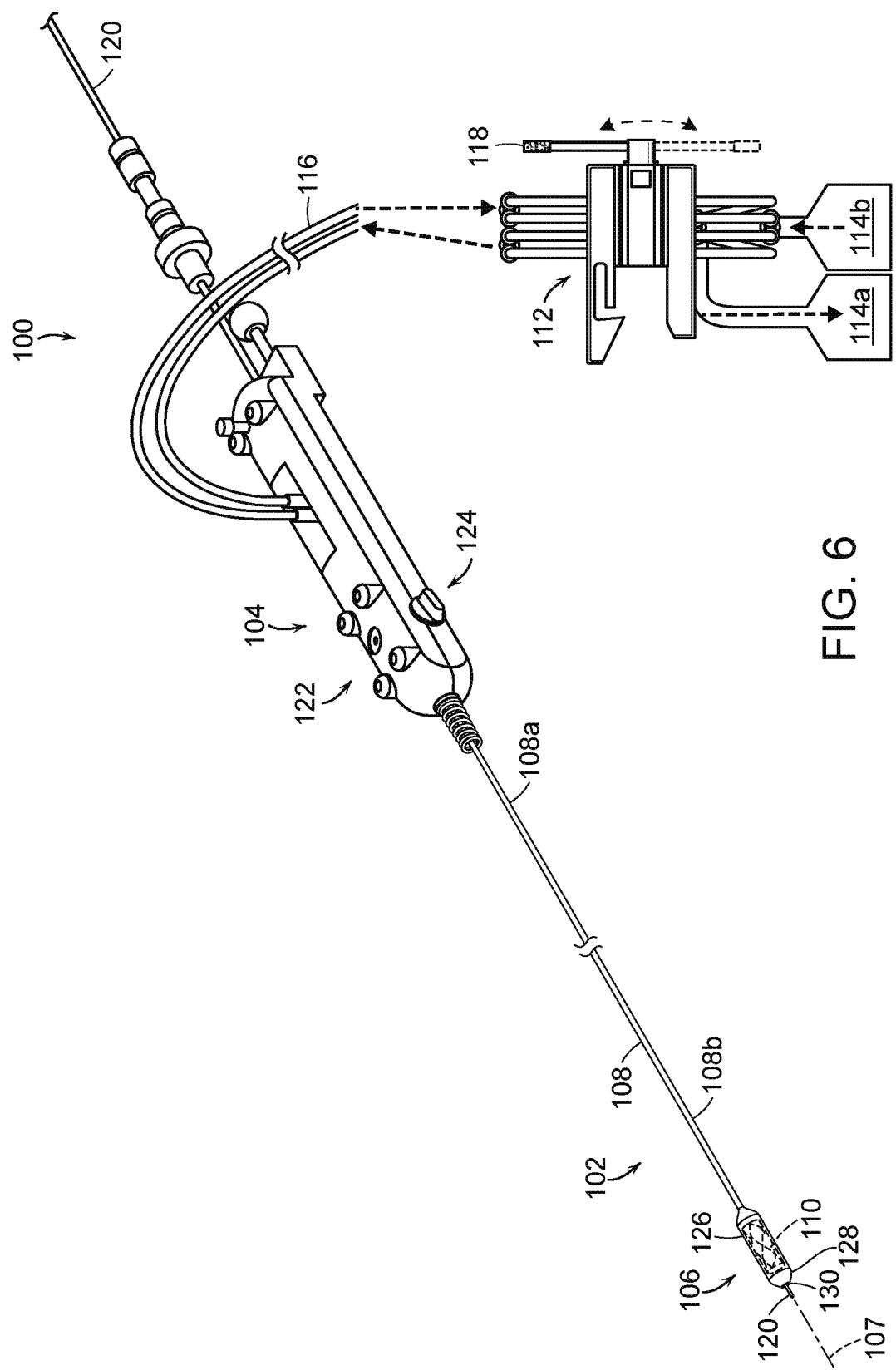
FIG. 6 is a partially schematic isometric view of a delivery system for deploying a prosthetic heart valve device in accordance with embodiments of the present technology.

FIG. 6 is a partially schematic isometric view of a hydraulic delivery system 100 ("system 100") for deploying a prosthetic heart valve device in accordance with embodiments of the present technology. The system 100 includes a catheter 102 with an elongated catheter body 108 and a delivery capsule 106. The catheter body 108 has a proximal portion 108a coupled to a handheld control unit 104 (e.g., a handle) and a distal portion 108b carrying the delivery capsule 106. The delivery capsule 106 can be configured to contain a prosthetic heart valve device 110 (shown schematically in broken lines). The control unit 104 can provide a steering capability (e.g., 360-degree rotation of the delivery capsule 106, 180-degree rotation of the delivery capsule 106, 3-axis steering, 2-axis steering) used to deliver the delivery capsule 106 to a target site (e.g., to a native mitral valve) and deploy the prosthetic heart valve device 110 at the target site. The catheter 102 can be configured to travel over a guidewire 120, which can be used to guide the delivery capsule 106 into the native heart valve. The system 100 also includes a fluid diversion device 112 configured to supply a flowable substance (i.e., a hydraulic fluid, such as water or saline) to the catheter 102 and receive the fluid from the catheter 102 to hydraulically move the delivery capsule 106 and deploy the prosthetic heart valve device 110.

The control unit 104 can include a control assembly 122 and a steering mechanism 124. For example, the control assembly 122 can include rotational elements, such as a handle, that can be rotated to rotate the delivery capsule 106 about its longitudinal axis 107. The control assembly 122 can also include features that allow a clinician to control the hydraulic deployment mechanisms of the delivery capsule 106 and/or the fluid diversion device 112. For example, the control assembly 122 can include buttons, handles, and/or other actuators that initiate unsheathing and/or resheathing of the prosthetic heart valve device 110. The steering mechanism 124 can be used to steer the catheter 102 through the anatomy by bending the distal portion 108b of the catheter body 108 about a transverse axis. In other embodiments, the control unit 104 may include additional and/or different features that facilitate delivering the prosthetic heart valve device 110 to the target site.

The delivery capsule 106 includes a housing 126 configured to carry the prosthetic heart valve device 110 in the containment configuration. The housing 126 can be made of one, two, or more components that at least partially enclose the prosthetic heart valve device 110 therein. The housing 126 can include a distal end portion 128 can have an opening 130 through which the guidewire 120 can be threaded to allow for guidewire delivery to the target site. As shown in FIG. 6, the distal end portion 128 can also have an atraumatic shape (e.g., a partially spherical shape, a frustoconical shape, blunt configuration, rounded configuration) to facilitate atraumatic delivery of the delivery capsule 106 to the target site. The housing 126 can be made of metal, polymers, plastic, composites, combinations thereof, or other materials capable of holding the prosthetic heart valve device 110.

When the distal portion 108b of the elongated catheter body 108 is delivered to a target location, the control unit 104 and/or the fluid diversion device 112 can be used to hydraulically drive the delivery capsule 106 from a containment configuration for holding the prosthetic heart valve device 110 towards a deployment configuration to partially or fully deploy and expand the prosthetic heart valve device 110 from the delivery capsule 106. For example, the delivery capsule 106 can be hydraulically driven towards the deployment configuration by supplying a flowable liquid to a chamber of the system 100 while also removing a flowable liquid from a separate chamber. These fluid chambers can be positioned in the delivery capsule 106, along the elongated catheter body 108, in the handheld control unit 104, and/or elsewhere in the system 100. The hydraulically controlled movement of the delivery capsule 106 is expected to reduce, limit, or substantially eliminate uncontrolled deployment of the prosthetic heart valve device 110 caused by forces associated with expansion of the prosthetic heart valve device 110, such as jumping, self-ejection, and/or other types of uncontrolled movement. For example, the delivery capsule 106 is expected to inhibit or prevent translation of the prosthetic heart valve device 110 relative to the catheter body 108 while at least a portion of the prosthetic heart valve device 110 expands.

The catheter 102 is also configured to partially or fully resheathe the prosthetic heart valve device 110 after partial deployment from the delivery capsule 106. For example, the delivery capsule 106 can be hydraulically driven back towards the containment configuration (e.g., recaptured) by transferring fluid into one chamber and removing fluid from another chamber in an opposite manner as that used for deployment. The reshcathing (also referred to as recapturing herein) ability allows a clinician to re-position the prosthetic heart valve device 110, in vivo, for redeployment within the mitral valve MV or remove the prosthetic heart valve device 110 from the patient after partial deployment. After full deployment of the prosthetic heart valve device 110, the delivery capsule 106 and the catheter 102 can be drawn proximally through a guide catheter for removal from the patient. After removing the catheter 102, it can be cleaned and used to deliver additional prosthetic devices or it can be discarded.

The fluid diversion device 112 is fluidically coupled to the catheter 102 via the fluid line(s) 116. The fluid diversion device 112 is also fluidically coupled to one or more reservoirs 114 (identified as a first reservoir 114a and a second reservoir 114b) that can contain a flowable substance (e.g., water, saline) used to hydraulically drive positioning of the prosthetic heart valve device 110 by controlling fluid flow into a chamber while removing fluid from another chamber of the system 100. The reservoirs 114 may include an inflator device with pressurized fluid and a drain configured to receive drained fluid. The fluid diversion device 112 can include one or more hoses, tubes, or other components (e.g., fittings, connectors, valves) through which a fluid can pass from the reservoir(s) to the catheter 102, and/or through which the fluid can drain from the catheter 102 to the reservoir(s).

In some embodiments, the fluid lines 116 can deliver fluid to the catheter 102 from the second reservoir 114b via the fluid diversion device 112. The fluid lines 116 can also drain fluid from the catheter 102 to the first 114a via the fluid diversion device 112. In some embodiments, the fluid source may include one or more pressurization devices (e.g., inflator device, pump) fluidically coupled to the fluid diversion device 112, which can also include one or more fluid connectors, fittings, valves, and/or other fluidic components that facilitate moving the fluid to and/or from fluid reservoirs 114. The movement of fluid to and from the fluid diversion device 112 can be used to deploy the prosthetic heart valve device 110 from the delivery capsule 106 and/or resheathe the prosthetic heart valve device 110 after at least partial deployment.

As explained in greater detail below, the fluid diversion device 112 includes a flow control component that controls fluid to and from the catheter 102. In some embodiments, the flow control component can be disposed within an elongated aperture (e.g., a bore) extending through the fluid diversion device housing and include one or more cams that can change the direction of fluid flow based on the rotation of the flow control component. Further, the fluid diversion device 112 can include an actuator, such as a handle 118, that allows a clinician to control deployment or resheathing of the prosthetic heart valve device 110 by rotating the cam. The handle 118 can be rotated to cause the cam(s) to occlude different tubes as a function of the angle of rotation of the handle 118. In particular, a number of tubes can traverse the cam(s) such that rotation of the cam(s) can occlude fluid flow through a first subset of tubes while leaving a second subset of tubes open. The handle 118 can be rotated again to rotate the cam(s) such that fluid flow through the second subset of tubes is occluded while the first subset of tubes is caused to open. This occlusion and opening of specific tubes extending through the fluid diversion device 112 can initiate fluid flow in opposite directions to effectuate deployment and resheathing.

In some embodiments, the fluid diversion device 112 is coupled to a controller (not shown) that can include, without limitation, one or more computers, central processing units, processing devices, microprocessors, digital signal processors (DSPs), and/or application-specific integrated circuits (ASICs). To store information, for example, the controller can include one or more storage elements, such as volatile memory, non-volatile memory, read-only memory (ROM), and/or random-access memory (RAM). The stored information can include, pumping programs, patient information, and/or other executable programs. The controller can further include a manual input device (e.g., a keyboard, a touch screen) and/or an automated input device (e.g., a computer, a data storage device, servers, network). In still other embodiments, the controller may include different features and/or have a different arrangement for controlling the flow of fluid into and out of the reservoirs 114.

Figure 7A:
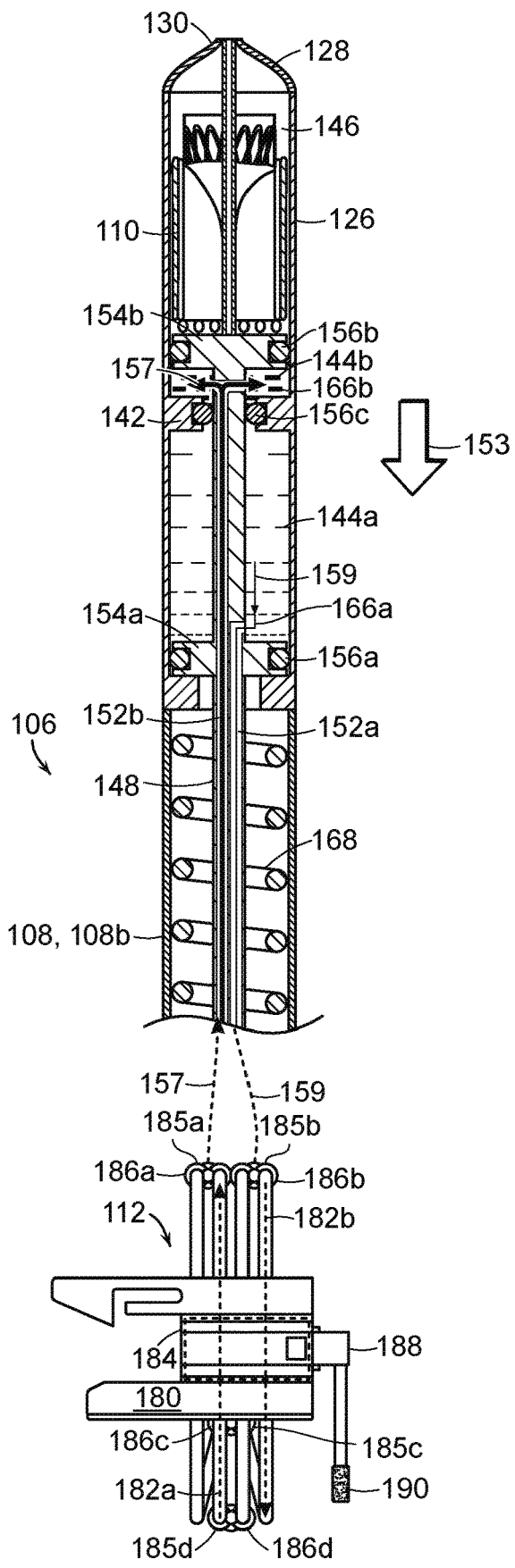
FIG. 7A is an enlarged partial cross-sectional view of the delivery system of FIG. 6 in a containment configuration in accordance with embodiments of the present technology.
Figure 7B:
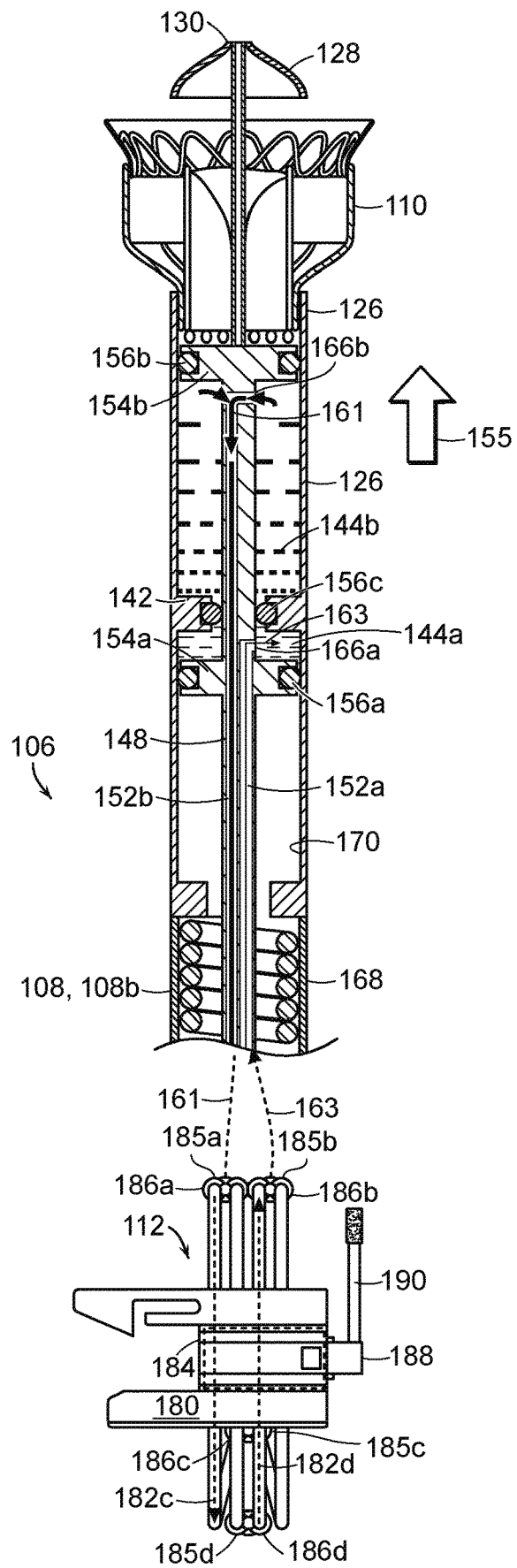
FIG. 7B is an enlarged partial cross-sectional view of the delivery system of FIG. 6 in a deployment configuration in accordance with embodiments of the present technology.

FIGS. 7A and 7B are enlarged partial cross-sectional views of the system 100 of FIG. 6 in a containment configuration (FIG. 7A) and a deployment configuration (FIG. 7B) in accordance with embodiments of the present technology. As shown in FIGS. 7A and 7B, the distal portion 108b of the elongated catheter body 108 carries the delivery capsule 106. The delivery capsule 106 includes the housing 126 and a platform 142 that together define, at least in part, a first chamber 144a and a second chamber 144b (referred to collectively as "the chambers 144"). The first chamber 144a and the second chamber 144b are fluidically sealed from each other and from a compartment 146 in the housing 126 that is configured to contain at least a portion of the prosthetic heart valve device 110. The chambers 144 can be filled and drained to hydraulically drive the delivery capsule 106 between the containment configuration (FIG. 7A) for holding the prosthetic heart valve device 110 and the deployment configuration (FIG. 7B) for at least partially deploying the prosthetic heart valve device 110. In some embodiments, the chambers 144 can be contained in combinations of the catheter body 108 and/or the handheld control unit 104. For example, the deployment chamber 144a may be positioned within the delivery capsule 106, whereas the recapture chamber 144b may be positioned along the catheter body 108 and/or within the handheld control unit 104.

As shown in FIG. 7A, the housing 126 of the delivery capsule 106 is urged proximally (in the direction of arrow 153) towards the deployment configuration when fluid is at least partially drained from the first chamber 144a (as indicated by arrow 159) while fluid is being delivered to the second chamber 144b (as indicated by arrow 157). The proximal translation of the housing 126 allows the prosthetic heart valve device 110 to at least partially deploy from the housing 126 (FIG. 7B) and expand such that it may engage surrounding tissue of a native mitral valve. As shown in FIG. 7B, the housing 126 is urged distally back towards the containment configuration to resheathe at least a portion of the prosthetic heart valve device 110 when fluid is at least partially drained from the second chamber 144b (as indicated by arrow 161) while fluid is being delivered into the first chamber 144a (as indicated by arrow 163).

The platform 142 extends at least partially between the inner wall of the housing 126 to divide the housing 126 into the first chamber 144a and the second chamber 144b. The platform 142 can be integrally formed as a part of the housing 126, such as an inwardly extending flange. Thus, the platform 142 can be made from the same material as the housing 126 (e.g., metal, polymers, plastic, composites, combinations thereof). In other embodiments, the platform 142 may be a separate component that at least partially separates the two chambers 144 from each other.

As shown in FIGS. 7A and 7B, a fluid delivery shaft 148 extends through the catheter body 108, into the housing 126 of the delivery capsule 106, and through the platform 142. At its proximal end (not shown), the shaft 148 is coupled to the fluid diversion device 112 and includes one or more fluid lines 152 (identified individually as a first line 152a and a second line 152b) that can deliver and/or drain fluid to and/or from the chambers 144. The fluid lines 152 can be fluid passageways or lumens integrally formed within the shaft 148, such as channels through the shaft itself, or the fluid lines 152 may be tubes or hoses positioned within one or more hollow regions of the shaft 148. The first line 152a is in fluid communication with the first chamber 144a via a first opening 166a in the first fluid line 152a, and the second line 152b is in fluid communication with the second chamber 144b via a second opening 166b in the second fluid line 152b. In other embodiments, the first and second chambers 144a and 144b can be in fluid communication with more than one fluid line. For example, each chamber 144 may have a dedicated fluid delivery line and dedicated fluid drain line.

The shaft 148 can also include a first flange or pedestal 154a and a second flange or pedestal 154b (referred to together as "flanges 154") that extend outwardly from the shaft 148 to define the proximal and distal ends of the first and second chambers 144a and 144b, respectively. Accordingly, the first chamber 144a is defined at a distal end by a proximal-facing surface of the platform 142, at a proximal end by a distally-facing surface of the first flange 154a, and by the interior wall of the housing 126 extending therebetween.

The second chamber 144b is defined at a proximal end by a distal-facing surface of the platform 142, at a distal end by a proximally-facing surface of the second flange 154b, and by the interior wall of the housing 126 extending therebetween. The compartment 146 containing the prosthetic heart valve device 110 can be defined by a distal-facing surface of the second flange 154b, the end cap 128, and the interior wall of the housing 126 extending therebetween. The shaft 148 and the flanges 154 can be integrally formed or separate components, and can be made from metal, polymers, plastic, composites, combinations thereof, and/or other suitable materials for containing fluids. The flanges 148 are fixed with respect to the shaft 148. Sealing members 156 (identified individually as first through third sealing members 156a-c, respectively), such as O-rings, can be positioned around or within the flanges 154 and/or the platform 142 to fluidically seal the chambers 144a-b from other portions of the delivery capsule 106. For example, the first and second sealing members 156a and 156b can be positioned in recesses of the corresponding first and second flanges 154a and 154b to fluidically seal the flanges 154 against the interior wall of the housing 126, and the third sealing member 156c can be positioned within a recess of the platform 142 to fluidically seal the platform 142 to the shaft 148. In other embodiments, the system 100 can include additional and/or differently arranged sealing members to fluidically seal the chambers 144.

The fluid lines 152 are in fluid communication with a fluid diversion device 112 at a proximal portion of the system 100. The fluid diversion device 112 has a housing 180 that includes channels (not shown) through a junction structure 184 (e.g., a bore). The housing 180 also includes tubes 182a-d disposed in the channels and coupled to fittings 186 (identified individually as fittings 186a-d, respectively) for the tubes 182a-d that traverse the junction structure 184. The fluid diversion device 112 includes a flow control component 188 (e.g., a shaft) including one or more cam(s) disposed at the junction structure 184. The flow control component 188 is rotationally movable to control fluid flow by occluding some of the tubes 182a-d and leaving others open. The fluid diversion device 112 can include a handle 190 operably coupled to move the flow control component 188 between a first position (e.g., containment or recapture configuration) and the second position (e.g., deployment configuration) to selectively allow fluid flow toward the first chamber and draining fluid from the second chamber, or vice versa. By rotating the handle 190 between two positions, the flow control component 188 can regulate fluid flow to and from the chambers 144.

As shown in FIG. 7A, when the flow control component 188 of the fluid diversion device 112 is placed in a first position (e.g., via a handle 190), the flow control component 188 defines selected fluid pathways via a plurality of tubes 182 (referred to individually as first through fourth tubes 182) to initiate device deployment. For example, in the first position the first tube 182a is open to allow fluid flow through the fittings 186c and 186a toward the second chamber 144b of the system 100, and the second tube 182b is also open to drain fluid from the first chamber 144a while the tube 182b allows fluid flow toward the second chamber 144b. In addition, the flow control component 188 can occlude the third and fourth tubes 182c and 182d via one or more cam(s) (not shown) to prevent fluid flow therethrough. The simultaneous or concurrent fluid delivery and removal via the first and second tubes 182a and 182b causes the delivery system 100 to move from the containment configuration to deployment configuration to at least partially deploy the prosthetic heart valve device 110 from the delivery capsule 106.

As shown in FIG. 7B, when the flow control component 188 is moved to a second position (via the handle 190), the cam is rotated such that the third tube 182c opens to allow fluid to drain from the second chamber 144b and the fourth tube 182d opens to allow fluid to flow through fittings 186d and 186b toward the first chamber 144a. This concurrent movement of fluid from the chambers 144 moves the delivery system 100 from the deployed or partially deployed configuration to the containment configuration, thereby enabling recapture of the prosthetic heart valve device 110.

Accordingly, movement of the fluid control component 188 between the first and second positions causes openings 185 (identified individually as first through fourth openings 185a-d) and the associated fittings 186 of the fluid diversion device 112 to alternatively serve as outlets and inlets depending on whether the delivery system 100 is moving toward a deployment configuration for unsheathing the prosthetic heart valve device 110 or toward the containment configuration for resheathing the prosthetic heart valve device 110. In the illustrated embodiment, for example, the first opening 185a and associated first fitting 186a serve as an outlet when the flow control component 188 is in the first position for device deployment and serves as an inlet when the flow control component 188 is in the second position for device recapture or system removal. Meanwhile, the second opening 185b and the second fitting 186b serve as an inlet when the flow control component 188 is in the first position and serve as an outlet when the flow control component 188 is in the second position. The third opening 185c and the associated third fitting 186c can serve as outlet regardless of whether the flow control component 188 is in the first or second position to provide a consistent fluid drainage site, and the fourth opening 185*d* and associated fitting 186*d* can serve as an inlet to supply fluid to one or both chamber 144 regardless of the position of the flow control component 188. This enables the third and fourth fittings 186*c* and 186*d* to maintain connections to a fluid retention or drainage reservoir and a fluid supply reservoir, respectively, throughout the delivery process. In other embodiments, the flow diversion device 112 can be configured such that direction of fluid through the third and fourth fittings 186*c* and 186*d* can be reversed based on positional changes of the fluid control component 188.

During use, the system 100 is arranged in the containment configuration (FIG. 7A) when the delivery capsule 106 is delivered to the target site at a native heart valve (e.g., via a transapical or trans-septal delivery approach). To fully or partially unsheathe the prosthetic heart valve device 110, the handle 190 is manipulated to move the fluid control component 188 to the first position. This allows fluid to flow along the first tube 182*a*, through the first fitting 186*a* (as indicated by arrow 157), to the second fluid line 152*b*, and into the second chamber 144*b*. As fluid is delivered to the second chamber 144*b*, fluid also drains through the first fluid line 152*a* from the first chamber 144*a*, toward the second fitting 186*b* (as indicated by arrow 159), and through the second tube 182*b*. In some embodiments, fluid is transferred to the second chamber 144*b* and from the first chamber 144*a* simultaneously and, optionally, in equal quantities so that the same amount of fluid transferred out of the first chamber 144*a* is transferred into the second chamber 144*b*. In some embodiments, different amounts of fluid are drained from and transferred to the chambers 144. This concurrent transfer of fluid between the chambers 144 drives the housing 126 proximally in the direction of arrow 153 to deploy the prosthetic heart valve device 110. In other embodiments, such as when one or both of the chambers 144 are positioned distal to the compartment 146 housing the prosthetic heart valve device 110, deployment can occur by moving the delivery capsule 106 in a distal direction.

In the deployment configuration of FIG. 7B, the delivery capsule 106 axially restrains an outflow portion of the prosthetic heart valve device 110 while an inflow portion of the prosthetic heart valve device 110 is deployed from the delivery capsule 106. After at least partial deployment, the fluid chambers 144 can be pressurized and drained in an inverse manner to move the housing 126 distally (in the direction of arrow 155) back toward the containment configuration and at least partially resheathe the prosthetic heart valve device 110. For resheathing, the handle 190 is manipulated to move the flow control component 188 to the second position. This allows fluid to drain from the second chamber 144*b*, through the second fluid line 152*b*, into the fitting 186*a* (as indicated by arrows 161), and along the third fluid tube 182*c*. As fluid exits the second chamber 144*b*, fluid is also delivered to the first chamber 144*a* via the second fitting 186*b* and to the first fluid line 152*a* (as indicated by arrows 163). Again, the fluid can be transferred simultaneously and/or in equal proportions from the two chambers 144. This transfer of fluid into the first chamber 144*a* and from the second chamber 144*b* drives the housing 126 distally in the direction of arrow 155 to controllably resheathe the prosthetic heart valve device 110 such that at least a portion of the prosthetic heart valve device 110 is again positioned within the compartment 146. This partial or full resheathing of the prosthetic heart valve device 110 allows a clinician to reposition or remove the prosthetic heart valve device 110 after partial deployment. The hydraulic movement of the housing 126 can provide controlled deployment and resheathing of the prosthetic heart valve device 110. In other embodiments, such as when one or both chambers 144 are positioned distal to the compartment 146 housing the prosthetic heart valve device 110, resheathing can occur by moving the delivery capsule 106 in a proximal direction.

As the delivery capsule 106 moves between the containment configuration and the deployment configuration, the housing 126 moves slideably with respect to the longitudinal axis of the shaft 148, while the prosthetic heart valve device 110 at least substantially maintains its longitudinal position relative to the catheter body 108. That is, the delivery capsule 106 can substantially prevent longitudinal translation of the prosthetic heart valve device 110 relative to the catheter body 108 while the prosthetic heart valve device 110 moves between the containment configuration (FIG. 7A) and the deployment configuration (FIG. 7B). This allows the clinician to position the sheathed prosthetic heart valve device 110 at the desired target site for deployment, and then deploy the device 110 at that target site without needing to compensate for any axial movement of the device 110 as it reaches full expansion (e.g., as would need to be taken into account if the device 110 was pushed distally from the housing 126).

As further shown in FIGS. 7A and 7B, the system 100 may also include a biasing device 168 that acts on the housing 126 to urge the housing 126 toward the containment configuration. The biasing device 168 compresses as the housing 126 moves to the deployment configuration (FIG. 7B) to apply more force on the housing 126 in a distal direction toward the containment configuration. In certain embodiments, the biasing device 168 acts continuously on the housing 126, urging it toward the containment configuration, and in other embodiments the biasing device 168 only acts on the housing 126 as it is compressed during deployment. In the illustrated embodiment, the biasing device 168 is positioned within the distal portion 108*b* of the catheter body 108, but in other embodiments the biasing device 168 can be positioned in other portions of the system 100, such as in the handheld control unit 104 (FIG. 6). The biasing device 168 can be a spring or other feature that urges the housing 126 and/or other portion of the delivery capsule 106 toward the containment configuration. The biasing device 168 limits or substantially prevents opening of the delivery capsule 106 attributable to the forces produced by the expanding prosthetic heart valve device 110. For example, an unsheathed portion of the prosthetic heart valve device 110 can expand outwardly from the partially opened delivery capsule 106 while the biasing device 168 inhibits further opening of the delivery capsule 106.

Figure 8:
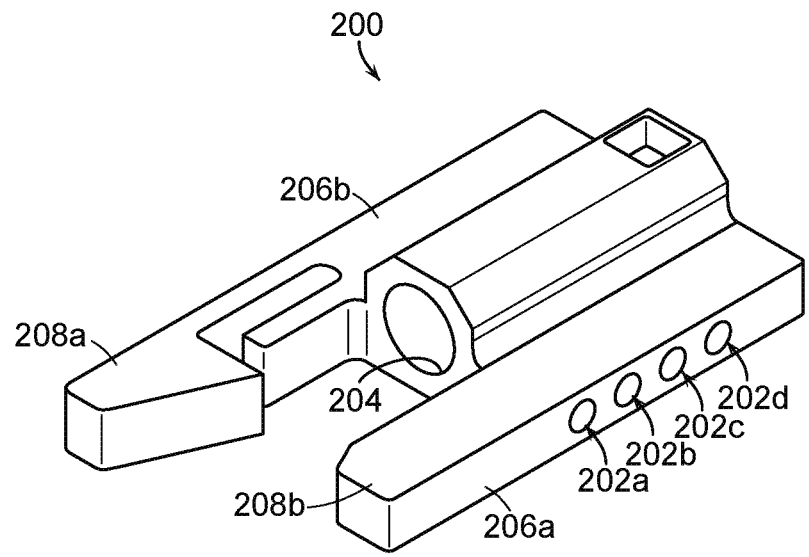
FIG. 8 is an isometric view of a housing of a fluid diversion device configured in accordance with embodiments of the present technology.

FIG. 8 is an isometric view of a fluid diversion device housing 200 ("housing 200") of a fluid diversion device (e.g., the fluid diversion device 112 of FIGS. 6-7B) configured in accordance with embodiments of the present technology. The housing 200 includes multiple channels 202 (identified individually as first through fourth channels 202*a-d*, respectively) and a junction structure 204 that extends laterally across the channels 202. The junction structure 204 can be defined by internal surfaces or walls of the housing 200 that create an aperture (e.g., a borehole) and/or a separate open tube or structure extending through a portion of the housing 200. Thus, the channels 202 traverse from a first side 206*a* of the housing 200 through the junction structure 204 to a second side 206*b* of the housing 200. The housing 200 can integrate components to collectively form a fluid diversion device for controlling fluid flow through a delivery system (e.g., delivery system 100 of FIGS. 6-7B) to deploy and/or recapture a prosthetic heart valve device (e.g., the prosthetic heart valve device 110 of FIGS. 6-7B), a cardiac repair device, and/or a medical device configured to be delivered elsewhere in the body. In some embodiments, the components are press-fit to the housing 200 to reduce or eliminate thread particulates and/or coated with a substance that reduces friction. The housing 200 can also include one or more connection structures 208 (identified individually as first and second connection structures 208a-b, respectively), such as brackets, that can receive and/or otherwise secure to another portion of the delivery system, such as an inflator device that contains fluid pressurized to flow towards selected chamber(s) of the delivery system. In some embodiments, the connection structures 208 can fasten to other features of the delivery system (e.g., other fluid reservoirs, the handheld controller (FIG. 6)) and/or structures separate from the delivery systems (e.g., procedure table, device holding tray, support poles).

Figure 9A:
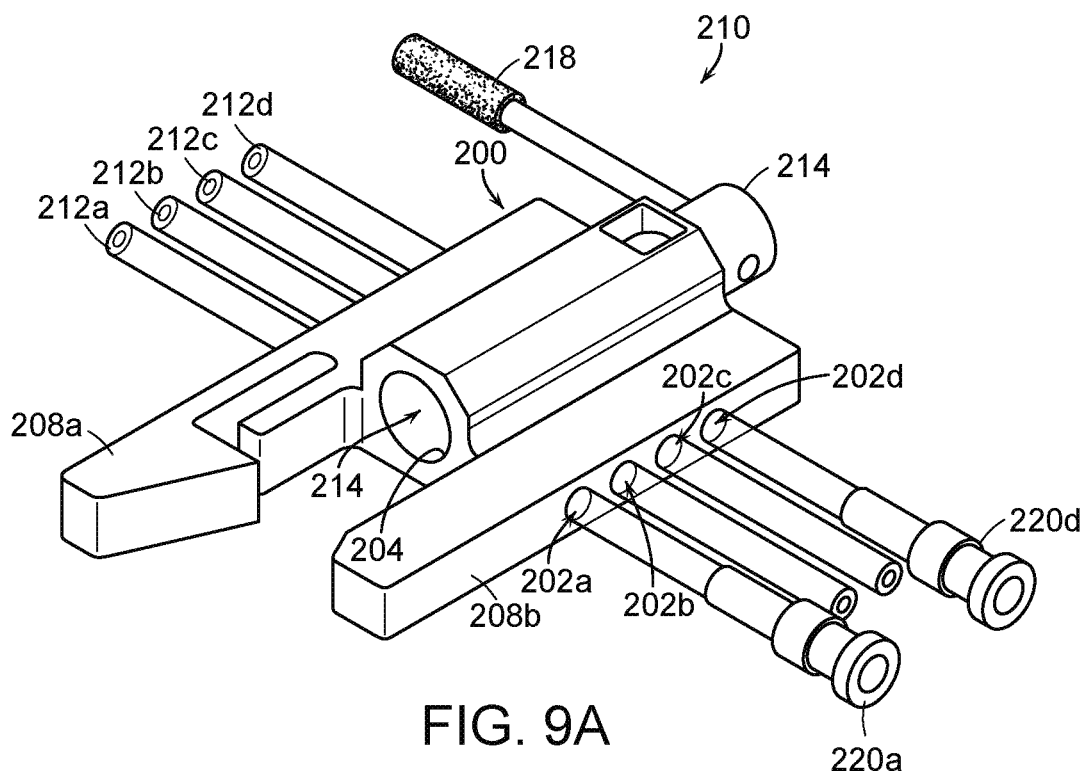
FIG. 9A is an isomeric view of a fluid diversion device including the housing of FIG. 8 configured in accordance with embodiments of the present technology.

FIG. 9A is an isomeric view of a fluid diversion device 210 including the housing 200 of FIG. 8 and associated fluid lines or tubes 212 (identified individually as first through fourth tubes 212a-d, respectively) configured in accordance with embodiments of the present technology. As shown in FIG. 9A, the channels 202 of the housing 200 receive the tubes 212 such that the tubes 212 extend from the first side 206a through the junction structure 204 to the second side 206b of the housing 200. A flow control component 214 is disposed in the junction structure 204, and includes one or more occlusion members, such as one or more cams 216 (described in further detail below with respect to FIG. 9C) that can selectively close or open subsets of the tubes 212 depending on the rotational position of the occlusion members. In the illustrated embodiment, the end portions of at least some of the tubes 212 are coupled to the fittings 220a and 220d that provide for connection to additional fluid lines and/or other components associated with the delivery system. In these and other embodiments, the tubes 212 can connect to other components, such as connectors, valves, reservoirs, pumps, other tubes, catheters, and/or other components associated with hydraulic delivery systems.

The fluid diversion device 210 can also include an actuator 218 operably coupled to the flow control component 214. In the embodiment illustrated in FIG. 9A, the actuator 218 is a rotatable handle that can be manipulated to rotate of the flow control component 214 to the deployment position, the recovery position, and/or other positions. Hence, rotation of the handle causes selective positioning of the occlusion members 216 in at least a first position that occludes a first subset of the tubes 212 and a second position that occludes a second subset of the tubes 212 for fluid communication in different directions relative to a first chamber (e.g., a deploy chamber) and a second chamber (e.g., a resheathe chamber) of the delivery system to facilitate deployment and recapture of the prosthetic heart valve device. Thus, the handle can be rotated between at least two positions (e.g., 180 degrees between first and second positions) to change the direction of fluid flow relative to delivery system chambers of a coupled to the fluid diversion device 210. In other embodiments, the actuator 218 can be a push button, switch, dial, and/or other component that is operably coupled to the flow control component 214 and actuated by a user (e.g., a clinician) to adjust the position of the flow control component 214. Further, the actuator 218 can be configured withstand mechanical loads applied by clinicians to change the position of the flow control component 214, while providing mechanical stability and reduced friction to decrease the overall effort needed to change the direction of fluid flow.

During operation, fluid can pass from a reservoir (e.g., one of the reservoirs 114 of FIG. 6) through a selected subset of the tubes 212 toward the delivery catheter (e.g., the catheter 102 of FIG. 6) while fluid is drained through one or more of the other tubes 212 to another reservoir. For example, the first and fourth tubes 212a and 212d can be coupled to a drain that receives fluid from the delivery system, and the second and third tubes 212b and 212c to an inflator device (e.g., an indeflator) or other reservoir containing a fluid pressurized that can be delivered to the chambers of the delivery system.

The fluid diversion device 210 can be made of a variety of materials. For example, the housing 200, the flow control component 214, the handle 218, and/or the fittings 220 can be made of a mechanically robust material, such as a rigid polymer, metal, alloys, etc. The tubes 212 can be made of a variety of mechanically robust, yet compressible materials, such as a flexible polymer. The diameter(s) of the channels 202 of the housing 200 and/or the tubes 212 received therein can be selected such that they facilitate suitable pressures and speeds of fluid delivery to the delivery catheter.

FIGS. 9B and 9C are top and side views, respectively, of the fluid diversion device 210 of FIG. 9A in a first state or configuration in accordance with embodiments of the present technology. As shown in FIGS. 9B and 9C, the channels 202 can be arranged at least substantially in parallel to each other as they extend through portions of the housing 200, the flow control component 214, and the junction structure 204 (through which the flow control component 214 extends). The tubes 212 are disposed in the channels 202 and coupled to fittings 222 (identified individually as first through fourth fittings 222a-d, respectively) that define inlets and/or outlets of the fluid diversion device 210. As further shown in FIG. 9C, the fluid control component 214 can include one or more occlusion members, such as cams 216 (identified individually as first through fourth cams 216a-d, respectively). In the illustrated embodiment, the fluid control component 214 includes four cams 216, but in other embodiments the fluid control component 214 can include one, two, three, or more than four cams 216 or other occlusion members for selectively opening and closing the tubes 212. The cams 216 may include separation structures that space apart the tubes 212 such that the tubes 212 remain aligned with the channels 202. The plurality of cams 216 can be in line with each other, though rotationally offset from neighboring cams to provide selective occlusion of the tubes based on the rotation of the fluid control component 214. In some embodiments, for example, the first and third cams 216a and 216c can define a first cam subset rotationally aligned with each other, and the second and fourth cams 216b and 216d can define a second cam subset that is rotationally offset from the first cam subset. During use, a user can rotate or otherwise manipulate the actuator 218, which in turn rotates the fluid control component 214 about its longitudinal axis, thereby moving the cams 216 (via the actuator 218) such that the subsets of cams 216 selectively occlude and/or open corresponding subsets of the tubes 212.

When the fluid diversion device 210 is in the deployment configuration shown FIGS. 9B and 9C, the flow control component 214 moves to a first position via rotation of the actuator 218. In the first position, the rotational position of the flow control component 214 relative to the channels 202 causes the first subset of cams 216 (first and third cams 216a and 216c) to open the first and third tubes 212a and 212c, while pinching closed the second and fourth tubes 212b and 212d. Thus, in the first position the cams 216 occlude the second and fourth tubes 212b and 212d to prevent fluid flow and allow the first and third tubes 212a and 212c to remain open and allow fluid flow therethrough. In this first position, the cams 216 of the fluid diversion device 210 create an open fluid pathway through the third tube 212c, which allows fluid to flow from a fluid reservoir (e.g., an inflator device), through the fourth fitting 222d, across the fluid diversion device housing 200, through the second fitting 222b on the opposite side of the housing 200, and into a chamber (e.g., a deploy chamber, the second chamber 156b of FIG. 7A) of the delivery catheter. Positioning the cams 216 of the fluid diversion device 210 in the first position also creates an open fluid pathway through the first tube 212a, which allows fluid to flow from another chamber (e.g., a resheathe chamber, the first chamber 156a of FIG. 7A) of the delivery catheter, through the first fitting 222a, across the housing 200, through the third fitting 222c at the opposite side of the housing 200 to a drain or other reservoir that receives fluid exiting the delivery system. Thus, the fluid diversion device 210 can provide for the concurrent delivery and removal of fluid from two chambers of the delivery system, which collectively causes unsheathing and deployment of the prosthetic heart valve device.

Figure 9E:
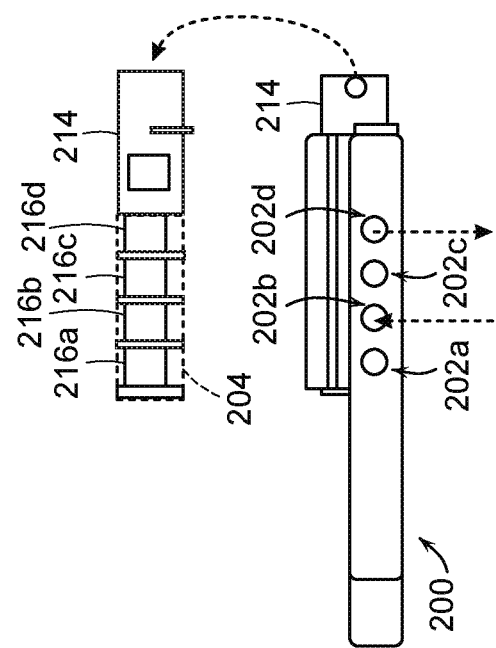
FIG. 9E is a side view of the fluid diversion device of FIG. 9D in the second configuration.
Figure 9D:
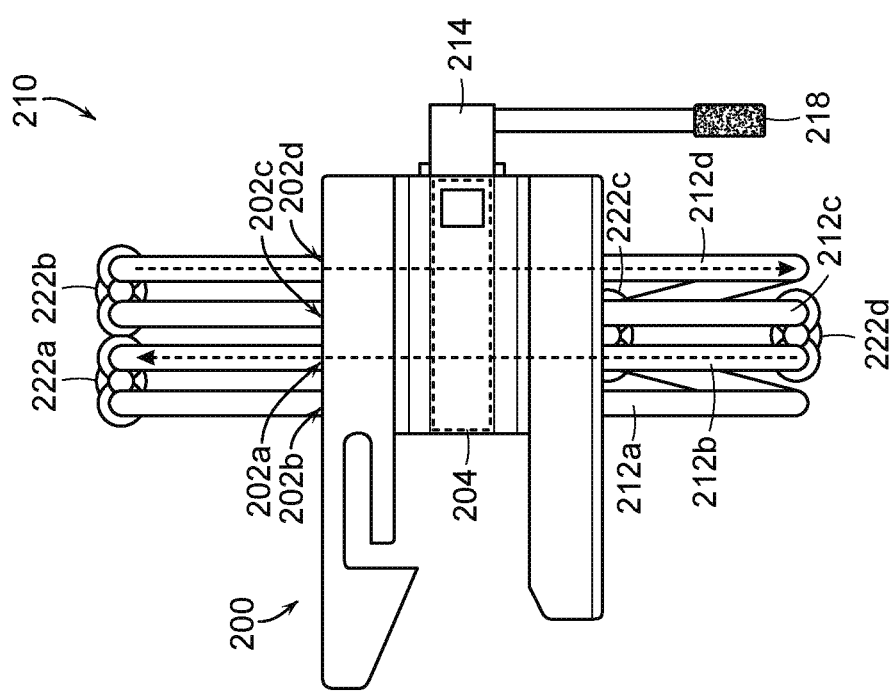
FIG. 9D is a top view of the fluid diversion device of FIG. 9A in a second configuration in accordance with embodiments of the present technology.

After at least partial deployment of the prosthetic heart valve device, the user can rotate the actuator 218 (e.g., 180 degrees) to move the flow control component 214 to a second position to allow for recapture of the prosthetic heart valve device (i.e., resheathing) and/or closure of the delivery capsule. For example, FIGS. 9D and 9E are top and side views, respectively, of the fluid diversion device 210 of FIG. 9A in a second state or configuration in accordance with embodiments of the present technology. In this second configuration, the flow control component 214 rotates to a second position relative to the channels 202, which causes the first subset of cams 216 to pinch or otherwise occlude the first and third tubes 212a and 212c, while the second subset of cams 216 allows fluid flow through the second and fourth tubes 212b and 212d.

In the second position, the cams 216 create an open fluid pathway through the second tube 212b, which allows fluid to flow from a fluid reservoir (e.g., the inflator device), through the fourth fitting 222d, across the housing 200, through the first fitting 222a, and into the resheathe chamber (e.g., the first chamber 156a of FIG. 7A) of the delivery catheter. Positioning the cams 216 of the fluid diversion device 210 in the section position also creates an open fluid pathway through the fourth tube 212d, which allows fluid to flow from the deploy chamber, through the second fitting 222, across the housing 200, through the third fitting 222c, and into the drain or other reservoir for receiving fluid. Thus, in operation, resheathing or closure of the delivery capsule occurs by fluid being delivered to the resheathe chamber via the second tube 212b, while fluid is drained from the deploy chamber via the fourth tube 212d.

In the embodiment illustrated in FIGS. 9A-9E, the second and third tubes 212b and 212c serve as fluid delivery pathways extending to either the deploy chamber or recapture chamber of the delivery catheter (depending upon the position of the fluid control component 214), and the fourth fitting 222d connected to the second and third tubes 212b and 212c serves as an inlet for the fluid delivery pathways. This is true when the fluid control component 214 is rotated to both the first position or the second position, and therefore the fourth fitting 222d and the second and third tubes 212b and 212c can be coupled to a fluid supply reservoir (e.g., an inflator device) to provide fluid for the delivery system chambers. Similarly, the first and fourth tubes 212a and 212d can serve as fluid removal pathways extending away from either the deploy chamber or recapture chamber of the delivery catheter, and the third fitting 222c connected thereto can serve as an outlet of the fluid removal pathways, regardless of the position of the flow control component 214. Therefore, the third fitting 222c and the first and fourth tubes 212a and 212d can be coupled to a drainage reservoir that receives fluid removed from the delivery system chambers or an opening that allows the fluid to flow out of the delivery system.

As further shown in FIGS. 9B-9E, the first fitting 222a can be coupled to the two tubes 212a, 212b in fluid communication with the resheathe chamber such that the first fitting forms an inlet through the first tube 212a or an outlet through second tube 212b depending on whether the flow control component 214 is in the first position or the second position. Similarly, the second fitting 222b can be coupled to the two tubes 212c, 212d in fluid communication with the deploy chamber such that the second fitting 222b forms an inlet through fourth tube 212d or an outlet through third tube 212c depending on whether the flow control component 214 is in the first position or the second position.

Although the fittings 222 and tubes 212 are described in terms of certain fluid directions through the fluid diversion device 210 depending on the position of the fluid control component 214, a person skilled in the art would understand that this is a relative arrangement that could be achieved with a different arrangement of components. For example, the description of the fluid flow of the fluid diversion device 210 can be changed by swapping the connections between the two fluid chambers of the delivery such that, for example, the recapture chamber is filled and the deploy chamber is drained when the flow control device 210 is in the first position. Moreover, although the fluid diversion device 210 is shown with four tubes 212 disposed in four channels 202, other embodiments can include fewer than four or more than four tubes 212 and/or channels 202.

Figure 10A:
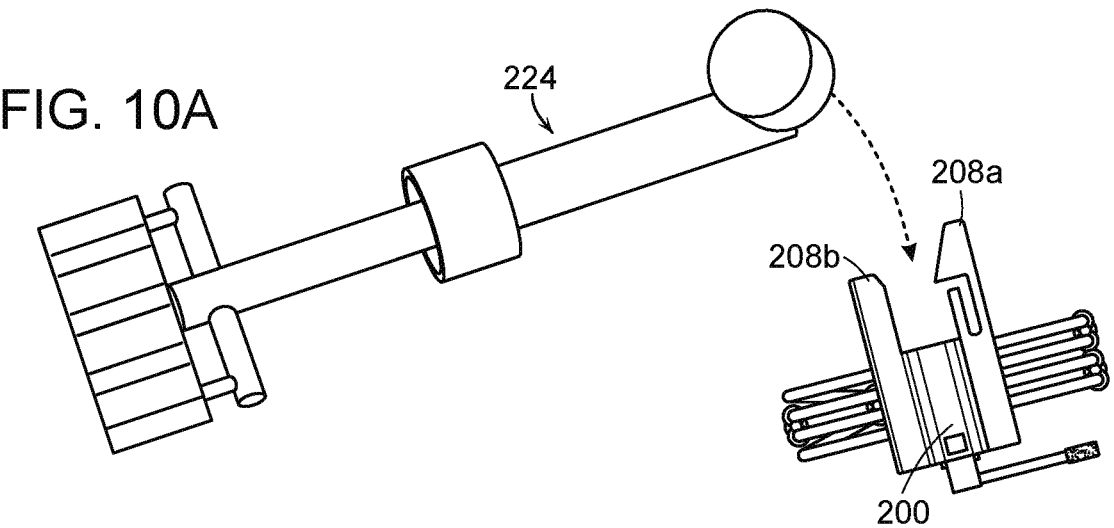
FIGS. 10A and 10B illustrate a process for attaching an inflator device to the fluid diversion device of FIG. 9A in accordance with embodiments of the present technology.
Figure 10B:
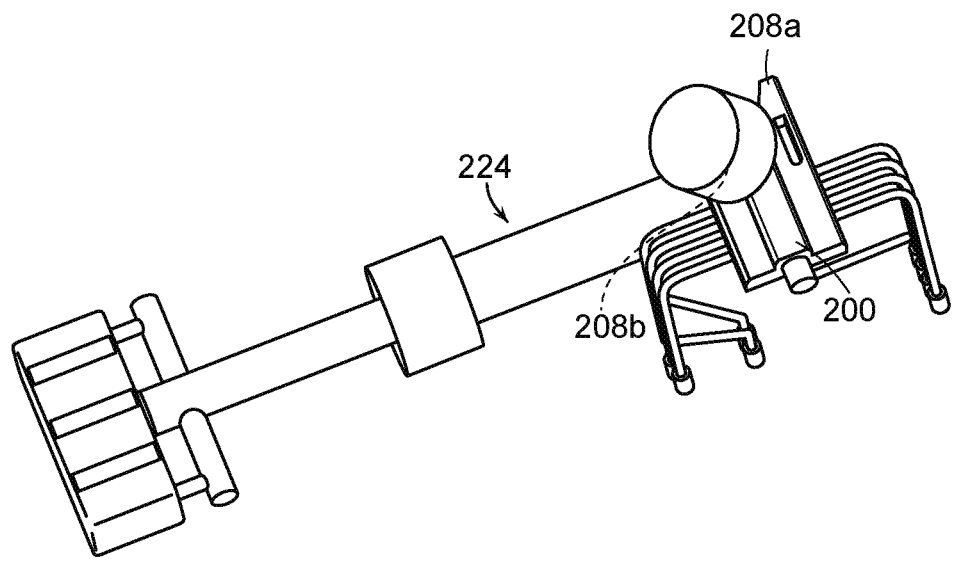

FIGS. 10A and 10B illustrate a process for attaching an inflator device 224 (e.g., an indeflator) to the housing 200 of the fluid diversion device 210 in accordance with embodiments of the present technology. As shown in FIG. 10A, the first and second bracket structures 208a and 208b that extend from the housing 200 can receive an end portion of the inflator device 224 (as indicated by the arrow). As shown in FIG. 10B, the inflator device 224 can mate with complimentary or interlocking surfaces of the bracket structures 208 to physically secure the inflator device 224 to the housing 200 during operation of the fluid diversion device 210. In some embodiments, the bracket structures 208 can include a knob that can be rotated or otherwise actuated to clamp the bracket structures 208 and/or another securing feature (e.g., a bolt) to the inflator device 224 to physically secure the two components together. In some embodiments, the fluid diversion device 210 can include additional or alternative connectors to secure the housing 200 to the inflator device 224.

Figure 11A:
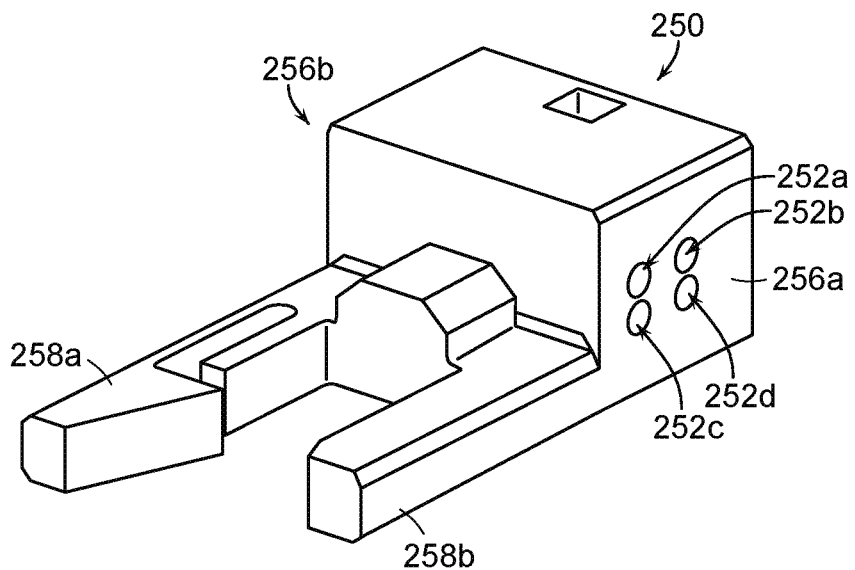
FIGS. 11A and 11B are a front and back isometric views, respectively, of a housing of a fluid diversion device configured in accordance with embodiments of the present technology.
Figure 11B:
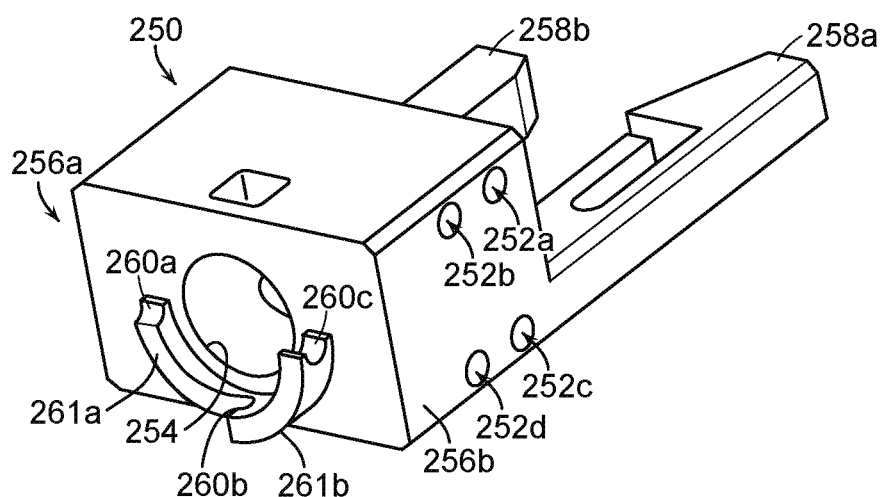

FIGS. 11A and 11B are front and back isometric views, respectively, of a fluid diversion device housing 250 ("housing 250") configured in accordance with embodiments of the present technology. The housing 250 can include certain features generally similar to the housing 200 described above with respect to FIGS. 8-10B. For example, the housing 250 includes a plurality of channels 252 (identified individually as first through fourth channels 252a-d, respectively) that extend between a first side 256a and a second side 256b of the housing 250, a junction structure 254 (e.g., an elongated aperture, a bore) that extends laterally across the channels 252, and bracket structures 258 (identified individually as a first bracket structure 258a and a second bracket structure 258b) that can releasably secure the housing 250 to an inflator device (e.g., an indeflator) and/or other structure associated with a delivery system. In the embodiment illustrated in FIGS. 11A and 11B, the channels 252 are arranged as two subsets forming two rows of channels 252: a first subset of channels 252 including the first and second channels 252a and 252b and a second subset of channels 252 including the third and fourth channels 252c and 252d. As described in further detail below with reference to FIG. 12B, the channels 252 in each subset are arranged in parallel with each other, but not necessarily in parallel with the channels 252 of the other subset. For example, the first subset of channels 252 may extend diagonally upward from the first side 256a to the second side 256b of the housing 250, and the second subset of channels 252 may extend diagonally downward from the first side 256a to the second side 256b, or vice versa. The housing 250 can integrate various components to collectively form a fluid diversion device operable to control fluid flow in a delivery system (e.g., the delivery system 100 of FIGS. 6-7B) to deploy or recapture a prosthetic heart valve device.

As shown in FIG. 11B, the housing 250 may further include a plurality of guide rails 261 (identified individually as first and second guide rails 261a and 261b, respectively) that terminate at one or more grooves or notches 260 (identified individually as first through third notches 260a-c, respectively). The notches 260 are configured to support a portion of a handle actuator (not shown) of a fluid diversion device at a plurality of rotationally offset positions (e.g., two or three different positions), and each position rotationally offset position defined by the notches 260 can correspond to a different mode of the fluid diversion device (e.g., a deployment mode, a recapture mode, and a neutral mode). For example, placing the handle actuator on the first notch 260a can set the fluid diversion device to a recapture configuration, placing the handle actuator on the second notch 260b can set the fluid diversion device to a neutral configuration, and placing the handle actuator on the third notch 260c can set the fluid diversion device to a deploy configuration.

Figure 12A:
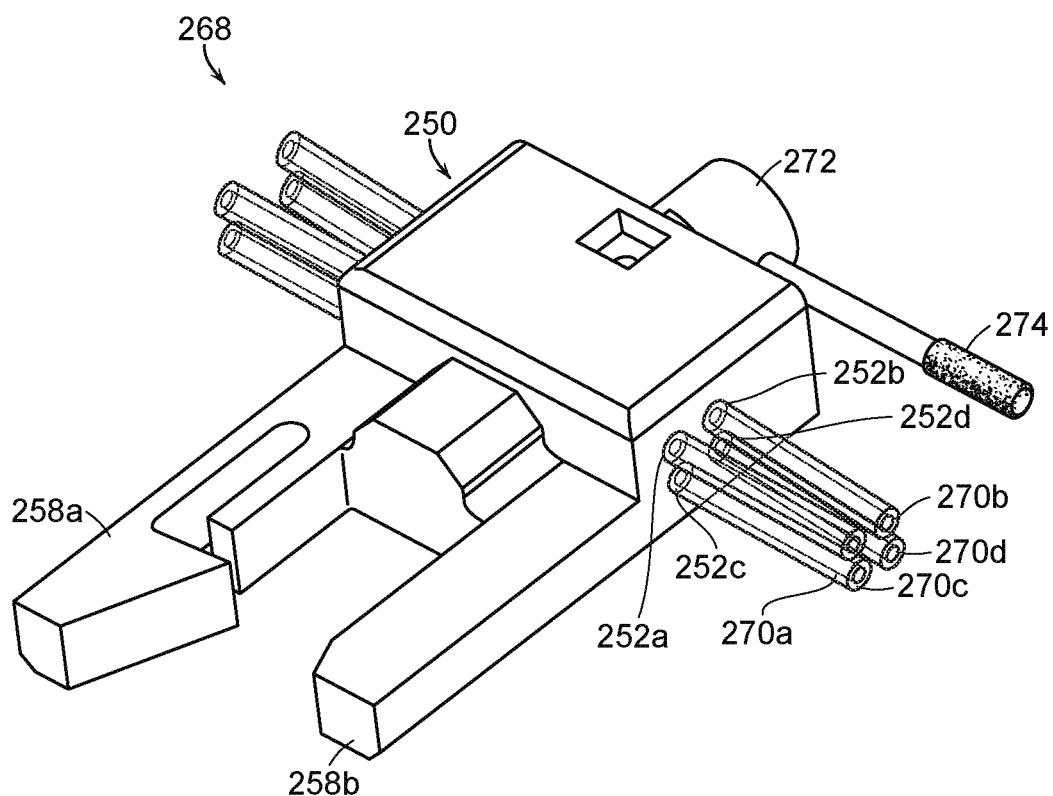
FIG. 12A is an isomeric view of the fluid diversion device of FIGS. 11A-11B and associated fluid lines configured in accordance with embodiments of the present technology.

FIG. 12A is an isometric view of a fluid diversion device 268 including the housing 250 of FIGS. 11A and 11B configured in accordance with embodiments of the present technology, and FIG. 12B is a partially transparent isometric view illustrating internal features of the fluid diversion device of FIG. 12A. The fluid diversion device 268 can include various features generally similar to the features of the fluid diversion device 210 described above with respect to FIGS. 9A-10B. For example, the fluid diversion device 268 includes a plurality of fluid lines or tubes 270 (identified individually as first through fourth tubes 270a-d, respectively) received in corresponding channels 252, a flow control component 272 extending through the junction structure 254 (FIG. 11B), and a handle actuator 274 coupled to the flow control component 272. The tubes 270 can include or be coupled to fittings (e.g., the fittings 222 of FIGS. 9B-9E) that form inlets and/or outlets of the fluid diversion device 268 to deliver fluid to/from deploy and recapture chambers of a delivery catheter (e.g., the delivery catheter device of FIGS. 6A-7B).

In operation, the fluid diversion device 268 can alternatively occlude fluid flow through a subset of the tubes 270, while allowing fluid flow through another subset of the tubes 270 by rotating the flow control component 272 in a manner similar to the fluid diversion device 210 described above with respect to FIGS. 9A-9E. For example, the handle actuator 274 can be rotated between at least two positions to change the direction of fluid flow relative to two chambers of the delivery catheter coupled to the fluid diversion device 268. However, unlike the fluid diversion device 210 of FIGS. 9A-9E that includes a plurality of cams that selectively act on subsets of tubes 212 arranged in parallel, the fluid control component 272 of the fluid diversion device 268 shown in FIG. 12A includes a single cam that acts on tubes arranged on opposite sides of the cam 276. The cam 276 (FIG. 12B) can close and open subsets of the tubes 270 by rotating the flow control component 272 to first and second positions. For example, moving the handle actuator 274 to the third notch 260c causes the flow control component 272 to rotate to the first position. In this first position, the flow control component 272 occludes fluid flow through the first and second tubes 270a and 270b, while allowing fluid flow through the third and fourth tubes 270c and 270d. Moving the handle actuator 274 to the first notch 260a causes the flow control component 272 to the second position in which the cam 276 occludes fluid flow through third and fourth tubes 270c and 270d and allows fluid flow through the first and second tubes 270a and 270b. Hence, the fluid diversion device 268 can be switched between a first configuration (e.g., a deploy configuration) and a second configuration (e.g., a recapture configuration) by rotating the fluid control component 272 to the first or second positions, respectively.

Figure 12C:
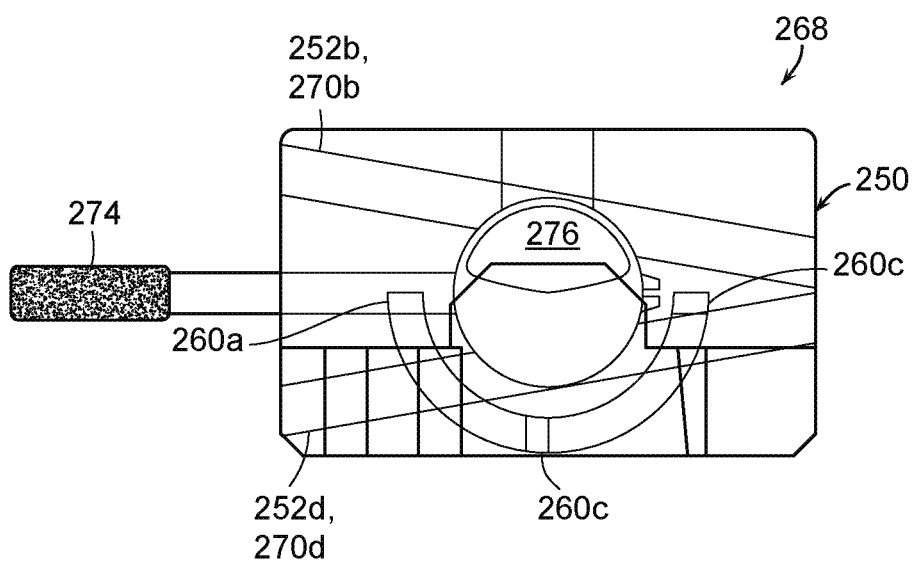
FIG. 12C is a partially transparent side view of the fluid diversion device of FIG. 12B in the first configuration.
Figure 12D:
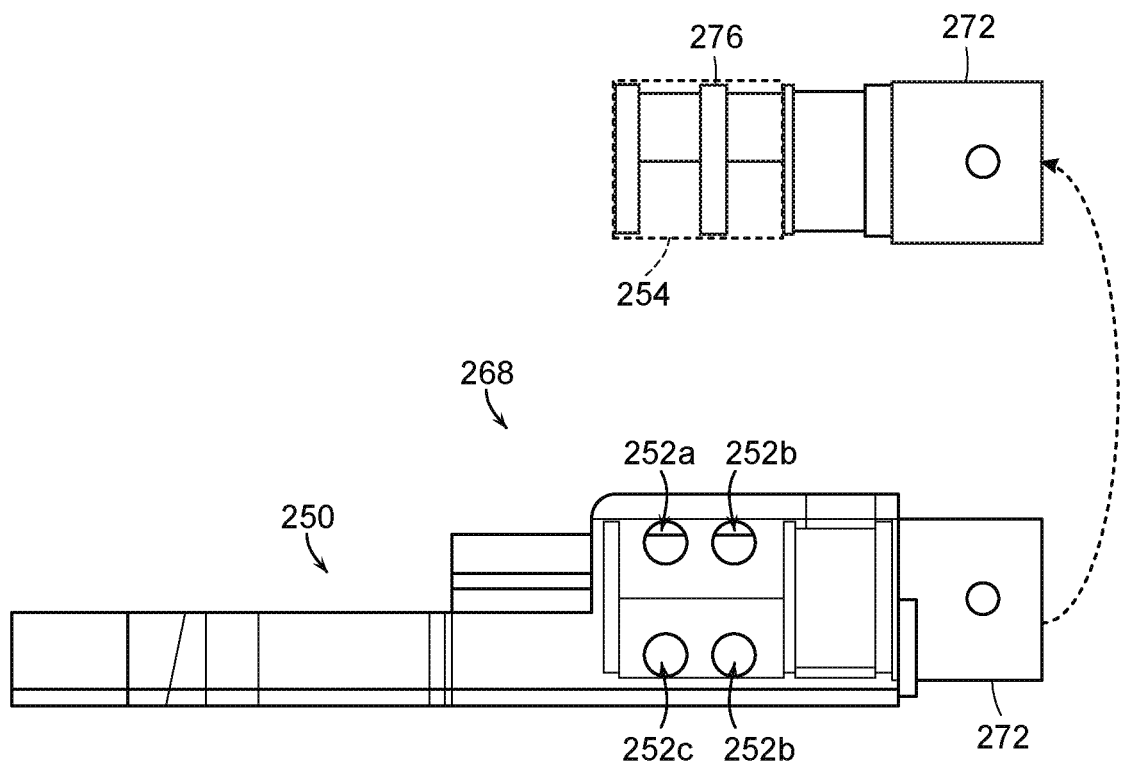
FIG. 12D is a partially transparent side view of the fluid diversion device of FIG. 12B in the first configuration.
Figure 12E:
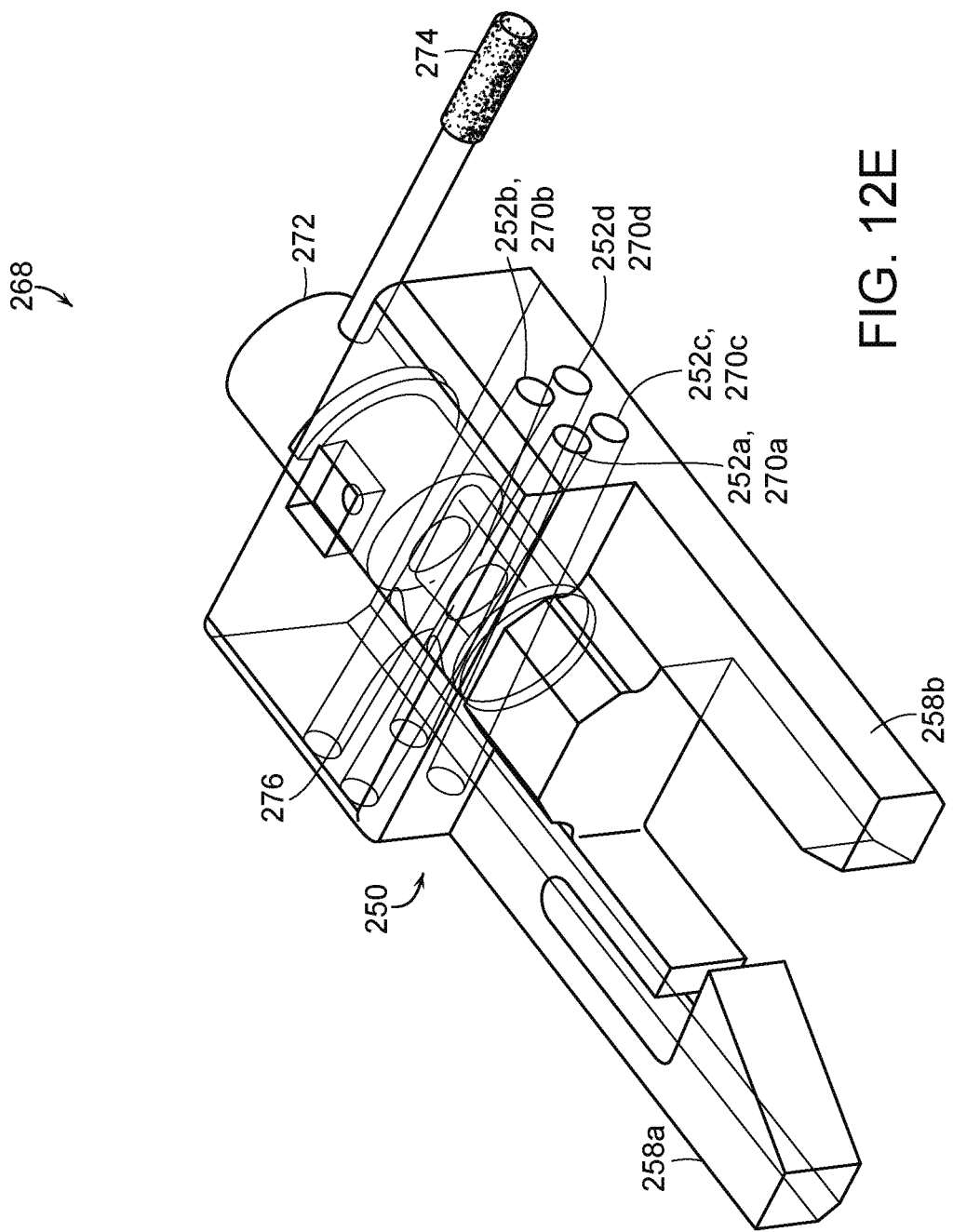
FIG. 12E is a partially transparent isomeric view of the fluid diversion device of FIG. 12A in a second configuration in accordance with embodiments of the present technology.
Figure 12F:
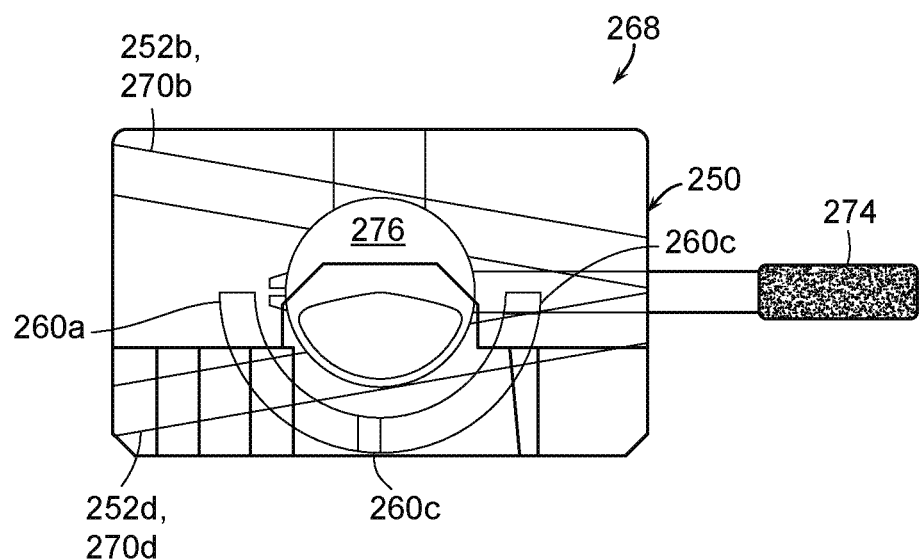
FIG. 12F is a partially transparent side view of the fluid diversion device of FIG. 12E in the second configuration.
Figure 12G:
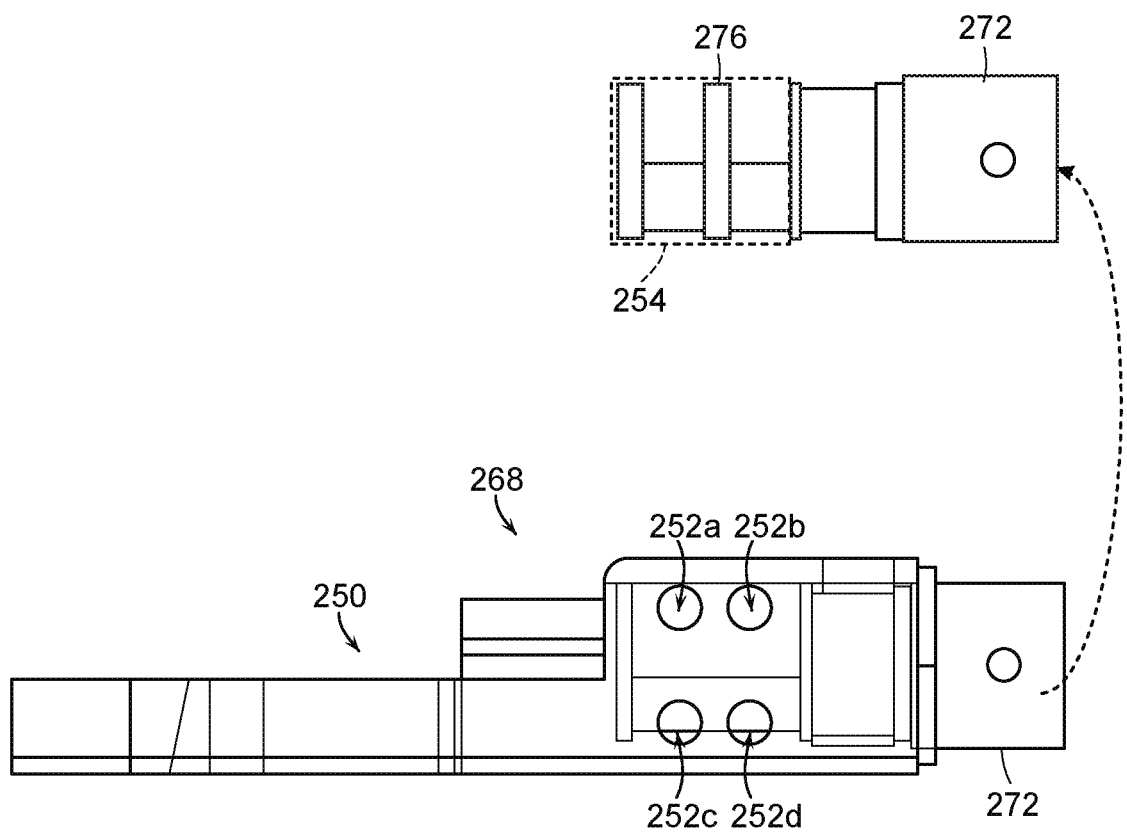
FIG. 12G is a partially transparent side view of the fluid diversion device of FIG. 12E in the second configuration.

FIGS. 12B-12D are partially transparent isomeric, back, and side views, respectively, of the fluid diversion device 268 of FIG. 12A in a first state or configuration (e.g., a deploy configuration), and FIGS. 12E-12G are partially transparent isomeric, back, and side views, respectively, of the fluid diversion device 268 of FIG. 12A in a second state or configuration (e.g., a recapture configuration). When the fluid diversion device 268 is in the first state shown in FIGS. 12B-12D, the fluid control component 272 is in the first position such that the first and second channels 252a and 252b (i.e., the first subset of channels 252) are occluded by the cam 276 to prevent fluid flow through the first and second tubes 270a and 270b, while the third and fourth channels 252c and 252d are open to allow fluid flow through the third and fourth tubes 270c and 270d. The third and fourth tubes 270c and 270d can define a fluid pathway between a fluid reservoir (e.g., an indeflator) and the deploy chamber and a second fluid pathway between the resheathe chamber and a fluid drain. Thus, when the fluid control component 272 is in the first position, fluid can be delivered to the deploy chamber via the third or fourth tube 270c,d and channel 252c,d, while fluid simultaneously drains from the resheathe chamber through the other of the tubes 270c,d and channels 252c,d. As shown in FIG. 12D, the cam 276 can also include structures, such as protrusions, to align the tubes 270 with the channels 252 and separate the tubes 270 from each other.

To change the fluid diversion device 268 to the second state shown in FIGS. 12E-12G, the user can rotate the handle actuator 274 a predetermined amount (e.g., 180-degrees) such that the handle actuator 274 is supported by the first notch 260a. This rotation of the handle actuator 274 rotates the fluid control component 272 to the second position in which the cam 276 opens the first and second channels 252a and 252b to allow fluid flow through the first and second tubes 270a and 270b, while occluding the channels third and fourth 252c and 252d to prevent fluid flow through the third and fourth channels 270c and 270d. The first and second tubes 270a and 270b can form a fluid pathway between a fluid reservoir (e.g., an indeflator) and the resheathe chamber and a second fluid pathway between the deploy chamber and a fluid drain. Thus, when the fluid control component 272 is in the second position, fluid can be delivered to the resheathe chamber via the first or second tube 270a,b and channel 252a,b, while fluid simultaneously drains from the deploy chamber through the other of the tubes 270a,b and channels 252a,b. Accordingly, the clinician can change the position of the fluid control component 272 by rotating the handle actuator 274 to form a combination of the different fluid pathways through the tubes 270 based on the rotational position of the fluid control component 272.

The fluid diversion device 268 can optionally include one or more additional or other configurations, beyond the deploy and recapture configurations. For example, FIG. 12H is a partially transparent back view of the fluid diversion device 268 of FIG. 12A in a third state or configuration in accordance with embodiments of the present technology. The third configuration may be a neutral configuration in which the flow control component 272 is rotated a predetermined degree of rotation (e.g., 90-degrees counter-clockwise) from the deploy configuration. For example, a portion of the handle actuator 274 can rest against the second notch 260b to position the flow control component 272 in a third position corresponding to the neutral configuration of the device 268. In this neutral mode, the cam 276 can partially compress all of the tubes 270 to allow all of the tubes 270 to be flushed (e.g., before a delivery procedure). In some embodiments, the arrangement of the guide rails 261 and/or other features of the fluid diversion device 268 prevent the flow control component 272 from returning to this neutral configuration during operation once the device 268 has been moved from this configuration to avoid this configuration during device delivery.

Figure 12I:
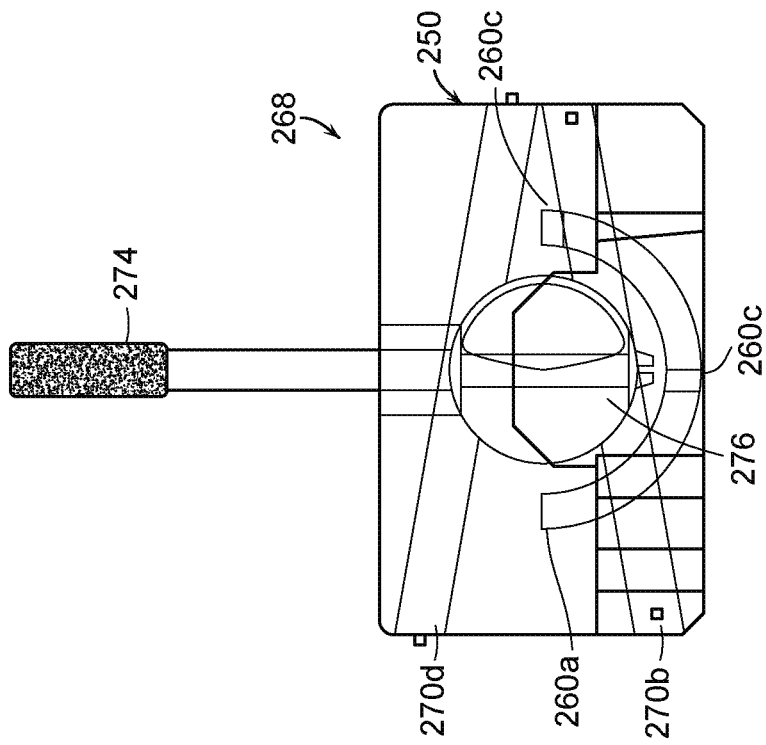
FIG. 12I is a partially transparent side view of the fluid diversion device of FIG. 12A in a fourth configuration in accordance with the second embodiment of the present technology.
Figure 12H:
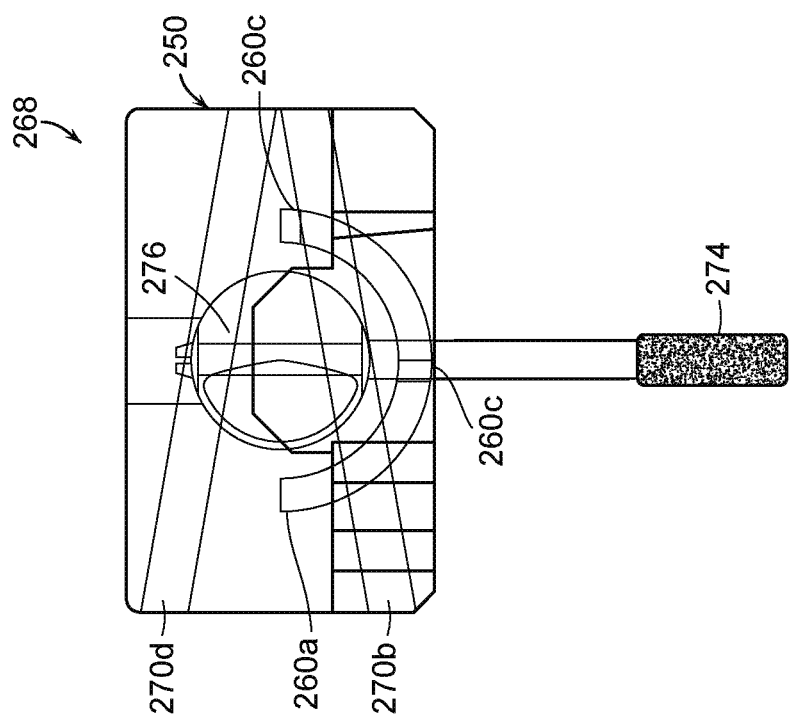
FIG. 12H is a partially transparent side view of the fluid diversion device of FIG. 12A in a third configuration in accordance with embodiments of the present technology.

FIG. 12I is a partially transparent back view of the fluid diversion device 268 of FIG. 12A in a fourth state or configuration in accordance with embodiments of the present technology. The fourth configuration may be used as a switchover mode in which the flow control component 272 is rotated a predetermined degree of rotation (e.g., 90-degrees clockwise) from the first state (e.g., deploy mode) toward the second state (e.g., recapture mode). During switchover, all of the tubes 270 may be compressed, which results in a reduced pressure drop when changing between the deployment and recovery configurations.

Although described in terms of configurations with inlets and outlets of the fluid diversion device to pass fluid in certain directions depending on the position of the flow control component, a person skilled in the art would understand that this is a relative arrangement that could be achieved with other arrangements of interconnections. For example, the description of the relative fluid flow can be changed by swapping connections between the two chambers such that, for example, the second chamber is filled and the first chamber is drained when the flow control component is in the first position. Moreover, although shown with four tubes disposed in four channels, other embodiments could include additional or fewer tubes or channels arranged in other orientations.

Although described with reference to applications that involve implanting prosthetic valve devices, the disclosed embodiments are not so limited. For example, embodiments of the disclosed fluid diversion devices described above with reference to FIGS. 6-12I can be configured to cause delivery of various other medical devices in addition, or alternative, to prosthetic valve devices for replacement of the mitral valve and/or other valves in the heart of the patient. Specific elements, substructures, advantages, uses, and/or other features described herein can be suitably interchanged, substituted or otherwise configured with one another. Furthermore, suitable elements of the embodiments described can be used as stand-alone and/or self-contained devices.

From the foregoing, it will be appreciated that specific embodiments of the invention have been described herein for purposes of illustration, but that various modifications may be made without deviating from the scope of the invention. Accordingly, the invention is not limited except as by the appended claims.

What is claimed is:

1. A fluid diversion device for controlling fluid flow in a delivery system to deploy a prosthetic heart valve device, the fluid diversion device comprising:
   a housing including a first side, a second side, a bore, and a plurality of channels traversing the housing from the first side through the bore to the second side, wherein the plurality of channels are configured to receive a corresponding plurality of tubes that extend from the first side through the bore to the second side of the housing, and wherein the bore extends laterally across the plurality of channels;
   an occlusion member disposed in the bore, wherein rotation of the occlusion member enables selective occlusion of either a first subset of tubes of the plurality of tubes or a second subset of tubes of the plurality of tubes disposed in the plurality of channels; and
   an actuator operably coupled to the occlusion member to enable selective positioning of the occlusion member in at least a first position that occludes the first subset of tubes and a second position that occludes the second subset of tubes for fluid communication in different directions relative to a first chamber and a second chamber of the delivery system to cause deployment and recapture of the prosthetic heart valve device.

2. The fluid diversion device of claim 1, wherein, when the occlusion member is in the second position, the first subset of tubes is open and the second subset of tubes is occluded to allow fluid to drain from the first chamber and to allow fluid to flow toward the second chamber.

3. The fluid diversion device of claim 2, wherein, when the occlusion member is in the first position, the first subset of tubes is occluded and the second subset of tubes is open to allow fluid to flow towards the first chamber and to allow fluid to drain from the second chamber.

4. The fluid diversion device of claim 3, wherein the delivery system is configured to cause deployment of the prosthetic heart valve device when the occlusion member is in the first position, and configured to cause recapture of the prosthetic heart valve device when the occlusion member is in the second position.

5. The fluid diversion device of claim 1, wherein the delivery system is configured to cause deployment of the prosthetic heart valve device when the occlusion member is in the first position, and configured to cause recapture of the prosthetic heart valve device when the occlusion member is the second position.

6. The fluid diversion device of claim 1, further comprising:
   a bracket structure configured to receive and hold an inflator device to the housing, wherein the inflator device contains fluid pressurized to flow towards the first chamber and the second chamber depending on whether the occlusion member is in the first position or the second position, respectively.

7. The fluid diversion device of claim 1, further comprising:
a first retention member configured to hold the actuator in a first position that sets the occlusion member in the first position, and
a second retention member configured to hold the actuator in a second position that sets the occlusion member in the second position.

8. The fluid diversion device of claim 7, wherein the actuator includes a handle operably coupled to the occlusion member to allow rotation of the occlusion member to the first position and the second position.

9. The fluid diversion device of claim 1, wherein any combination of the plurality of tubes is occluded to obstruct fluid flow through the plurality of tubes based on a position of the occlusion member.

10. The fluid diversion device of claim 1, wherein a rate of fluid flow in each tube of the plurality of tubes is proportional to an angle of rotation of the occlusion member.

11. The fluid diversion device of claim 1, wherein each channel of the plurality of channels are arranged in parallel to the other channels of the plurality of channels.

12. The fluid diversion device of claim 11, wherein the occlusion member comprises:
a first subset of cams; and
a second subset of cams arranged in series and rotationally offset relative to the first subset of cams such that the first subset of cams is configured to occlude the first subset of tubes while the second subset of cams opens the second subset of tubes.

13. The fluid diversion device of claim 1, wherein the plurality of channels comprises:
a first subset of channels arranged in parallel; and
a second subset of channels arranged in parallel, wherein the bore extends laterally between the second subset of channels and the first subset of channels.

14. The fluid diversion device of claim 13, wherein the occlusion member has only one cam configured to alternatively occlude the first subset of tubes disposed in the first subset of channels when the occlusion member is in the first position and occlude the second subset of tubes in the second subset of channels when the occlusion member is in the second position.

15. The fluid diversion device of claim 14, wherein, when the occlusion member is in a third position, the first subset of tubes and the second subset of tubes are occluded to prevent any fluid flow through the plurality of channels.

16. The fluid diversion device of claim 14, wherein, when the occlusion member is in a third position, each of the plurality of tubes is open to allow fluid flow through all the plurality of channels.

17. The fluid diversion device of claim 1, wherein the fluid diversion device is configured to be external to a patient during an implantation procedure of the prosthetic heart valve device.

18. A system for delivering a prosthetic heart valve device into a heart of a patient, the system comprising:
an elongated catheter body including a delivery control component that is hydraulically driven to deploy and recapture the prosthetic heart valve device relative to the heart of the patient;
a plurality of chambers including a first chamber and a second chamber operable to receive or expel fluid to hydraulically drive deployment and recapture of the prosthetic heart valve device; and
a fluid diversion device including:
a housing including a first side, a second side, a bore, and a plurality of channels traversing the housing from the first side through the bore to the second side, wherein the plurality of channels is configured to receive a corresponding plurality of tubes that extend from the first side through the bore to the second side of the housing, and wherein the bore extends laterally across the plurality of channels,
an occlusion member disposed in the bore, wherein rotation of the occlusion member enables selective occlusion of either a first subset of tubes of the plurality of tubes or a second subset of tubes of the plurality of tubes disposed in the plurality of channels, and
an actuator operably coupled to the occlusion member to enable selective positioning of the occlusion member in at least a first position that occludes the first subset of tubes and a second position that occludes the second subset of tubes for fluid communication in different directions relative to the first chamber and the second chamber to cause deployment and recapture of the prosthetic heart valve device.

19. The system of claim 18, wherein, when the occlusion member is in the second position, the first subset of tubes is open and the second subset of tubes is occluded to allow fluid to drain from the first chamber and to allow fluid to flow toward the second chamber.

20. The system of claim 19, wherein, when the occlusion member is in the first position, the first subset of tubes is occluded and the second subset of tubes is open to allow fluid to flow towards the first chamber and to allow fluid to drain from the second chamber.

21. The system of claim 20, further comprising:
a handle of the elongated catheter body, which contains the second chamber.

22. The system of claim 20, wherein the delivery control component contains the second chamber.

23. The system of claim 20, wherein the delivery control component contains the first chamber.

24. A fluid diversion device for controlling fluid flow in a delivery system to deploy a medical device, the fluid diversion device comprising:
a housing including a plurality of channels configured to receive a corresponding plurality of tubes, and a bore that extends laterally across the plurality of channels;
an occlusion member disposed in the bore, wherein rotation of the occlusion member selectively occludes either a first subset of tubes from the plurality of tubes or a second subset of tubes from the plurality of tubes; and
an actuator configured to enable rotation of the occlusion member to at least a first position and a second position such that the first subset of tubes and the second subset of tubes are alternatively occluded in the first position or the second position for fluid communication in different directions relative to a plurality of chambers of the delivery system operable to deploy and recapture the medical device.

* * * * *